(12) United States Patent
DeFreitas et al.

(10) Patent No.: US 12,042,134 B2
(45) Date of Patent: Jul. 23, 2024

(54) BREAST BIOPSY LATERAL ARM SYSTEM

(71) Applicant: Hologic, Inc., Marlborough, MA (US)

(72) Inventors: Kenneth F. DeFreitas, Patterson, NY (US); Thomas W. DeYoung, Hopewell Junction, NY (US); John Girgenti, New Milford, CT (US); Timothy R. Stango, Sandy Hook, CT (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 17/679,267

(22) Filed: Feb. 24, 2022

(65) Prior Publication Data

US 2022/0370052 A1   Nov. 24, 2022

Related U.S. Application Data

(63) Continuation of application No. 14/646,630, filed as application No. PCT/US2013/071139 on Nov. 21, (Continued)

(51) Int. Cl.
*A61B 5/00* (2006.01)
*A61B 5/145* (2006.01)
(Continued)

(52) U.S. Cl.
CPC .......... *A61B 10/0275* (2013.01); *A61B 5/708* (2013.01); *A61B 10/0233* (2013.01); (Continued)

(58) Field of Classification Search
None
See application file for complete search history.

(56) References Cited

U.S. PATENT DOCUMENTS

| 4,450,536 A | 5/1984 | Schroeder |
| 4,869,378 A | 9/1989 | Miller |

(Continued)

FOREIGN PATENT DOCUMENTS

| EP | 1410764 | 4/2004 |
| JP | 2004033753 | 2/2004 |

(Continued)

OTHER PUBLICATIONS

European Search Report in Application 17196855.5, mailed Apr. 17, 2018, 8 pages.

(Continued)

*Primary Examiner* — Benjamin S Melhus
(74) *Attorney, Agent, or Firm* — Merchant & Gould P.C.

(57) ABSTRACT

A breast biopsy lateral arm system includes a removable gun mount which attaches to a carriage that traverses along an X-axis defined by a lateral arm in order to position a biopsy needle relative to a patient. The carriage rides along the lateral arm on self-adjusting rollers which are loaded against the lateral arm by spring members. A cam-actuated carriage slide lock can be used to secure the carriage in a desired position relative to the lateral arm. A cam-actuated removable gun mount lock allows the gun mount to be quickly changed and offset orthogonally with respect to the X-axis. An X-axis stop can be used to establish a position to which the carriage can be returned with accuracy.

8 Claims, 21 Drawing Sheets

Related U.S. Application Data 2013, now Pat. No. 11,284,869, which is a continuation-in-part of application No. 13/611,502, filed on Sep. 12, 2012, now Pat. No. 9,308,017.

(60) Provisional application No. 61/729,141, filed on Nov. 21, 2012, provisional application No. 61/535,401, filed on Sep. 16, 2011.

(51) Int. Cl.

| | | |
|---|---|---|
| *A61B 5/15* | (2006.01) | |
| *A61B 5/151* | (2006.01) | |
| *A61B 5/157* | (2006.01) | |
| *A61B 10/02* | (2006.01) | |
| *A61B 90/11* | (2016.01) | |
| *A61B 90/17* | (2016.01) | |

(52) U.S. Cl.
 CPC .............. *A61B 90/11* (2016.02); *A61B 90/17* (2016.02); *A61B 2010/0208* (2013.01)

(56) References Cited

U.S. PATENT DOCUMENTS

| | | | |
|---|---|---|---|
| 4,875,478 A * | 10/1989 | Chen | A61B 6/0414 378/20 |
| 4,879,508 A | 11/1989 | Andermo | |
| 5,047,036 A | 9/1991 | Koutrouvelis | |
| 5,053,042 A | 10/1991 | Bidwell | |
| 5,078,140 A | 1/1992 | Kwoh | |
| 5,249,583 A | 10/1993 | Mallaby | |
| 5,280,427 A | 1/1994 | Magnusson et al. | |
| 5,308,352 A | 5/1994 | Koutrouvelis | |
| 5,316,014 A | 5/1994 | Livingston | |
| 5,320,111 A | 6/1994 | Livingston | |
| 5,494,039 A * | 2/1996 | Onik | A61B 17/3403 600/562 |
| 5,594,769 A * | 1/1997 | Pellegrino | A61B 90/17 378/208 |
| 5,628,327 A | 5/1997 | Unger et al. | |
| 5,665,095 A | 9/1997 | Jacobson | |
| 5,769,086 A * | 6/1998 | Ritchart | A61B 10/0275 600/566 |
| 5,782,775 A | 7/1998 | Milliman | |
| 5,928,219 A * | 7/1999 | Friend | A61B 17/3403 606/1 |
| 6,030,348 A | 2/2000 | Unger | |
| 6,102,866 A | 8/2000 | Nields et al. | |
| 6,270,506 B1 * | 8/2001 | Sittek | A61B 90/17 606/130 |
| 6,331,437 B1 | 12/2001 | Cohen | |
| 6,447,447 B1 | 9/2002 | Mitsumori | |
| 6,464,648 B1 | 10/2002 | Nakamura | |
| 6,468,226 B1 | 10/2002 | McIntyre, IV | |
| 6,487,434 B1 * | 11/2002 | Kaiser | A61B 90/17 600/568 |
| 6,665,554 B1 | 12/2003 | Charles et al. | |
| 6,712,773 B1 | 3/2004 | Viola | |
| 7,438,692 B2 | 10/2008 | Tsonton et al. | |
| 8,123,697 B2 | 2/2012 | Daum et al. | |
| 8,932,233 B2 | 1/2015 | Haberstitch | |
| 8,945,014 B2 | 2/2015 | Zan | |
| 9,308,017 B2 | 4/2016 | Girgenti | |
| 9,314,926 B2 | 4/2016 | Bailey | |
| 9,937,016 B2 | 4/2018 | Girgenti | |
| 11,259,891 B2 | 3/2022 | Girgenti | |
| 11,284,869 B2 | 3/2022 | DeFreitas | |
| 2001/0011156 A1 * | 8/2001 | Viola | A61B 10/0275 600/568 |
| 2001/0039378 A1 * | 11/2001 | Lampman | A61B 5/055 600/410 |
| 2002/0065462 A1 | 5/2002 | Brabrand et al. | |
| 2002/0151820 A1 | 10/2002 | Dvorak | |
| 2002/0156376 A1 | 10/2002 | Wang | |
| 2003/0073895 A1 | 4/2003 | Nields et al. | |
| 2003/0199785 A1 | 10/2003 | Hibner et al. | |
| 2004/0077972 A1 | 4/2004 | Tsonton et al. | |
| 2005/0085838 A1 | 4/2005 | Thompson | |
| 2005/0261581 A1 | 11/2005 | Hughed | |
| 2005/0283069 A1 * | 12/2005 | Hughes | A61B 17/3417 600/407 |
| 2006/0241385 A1 | 10/2006 | Dietz | |
| 2006/0261571 A1 | 11/2006 | Mitchell | |
| 2007/0016067 A1 | 1/2007 | Webster, III et al. | |
| 2007/0032723 A1 | 2/2007 | Glossop | |
| 2008/0045833 A1 | 2/2008 | Defreitas et al. | |
| 2009/0030339 A1 | 1/2009 | Cheng et al. | |
| 2009/0131824 A1 | 5/2009 | Andrisek | |
| 2009/0171244 A1 | 7/2009 | Ning et al. | |
| 2009/0323892 A1 | 12/2009 | Hitzke | |
| 2010/0036245 A1 | 2/2010 | Yu et al. | |
| 2010/0113970 A1 * | 5/2010 | Okada | A61B 10/0266 600/562 |
| 2010/0160810 A1 | 6/2010 | Parihar | |
| 2010/0168723 A1 | 7/2010 | Suarez et al. | |
| 2010/0249647 A1 * | 9/2010 | Nakayama | A61B 90/17 600/567 |
| 2010/0249648 A1 * | 9/2010 | Nakata | A61B 90/11 378/37 |
| 2011/0015517 A1 | 1/2011 | Hughes | |
| 2011/0021947 A1 * | 1/2011 | Nakayama | A61B 6/469 378/37 |
| 2011/0087132 A1 | 4/2011 | DeFreitas et al. | |
| 2011/0112540 A1 | 5/2011 | McLean | |
| 2011/0118625 A1 | 5/2011 | Akuzawa et al. | |
| 2011/0301414 A1 | 12/2011 | Hotto et al. | |
| 2012/0007863 A1 | 1/2012 | Endo et al. | |
| 2012/0010512 A1 | 1/2012 | O'Laughlin et al. | |
| 2012/0053455 A1 * | 3/2012 | Okada | A61B 6/502 378/98.5 |
| 2012/0095329 A1 * | 4/2012 | Kamiya | G09B 23/30 600/566 |
| 2012/0277625 A1 * | 11/2012 | Nakayama | A61B 6/0414 250/393 |
| 2012/0298820 A1 | 11/2012 | Manolidis | |
| 2013/0072816 A1 | 3/2013 | Girgenti | |
| 2013/0108138 A1 * | 5/2013 | Nakayama | A61B 10/0233 382/132 |
| 2013/0158565 A1 | 6/2013 | Anvari | |
| 2015/0313674 A1 | 11/2015 | DeFreitas et al. | |
| 2016/0296298 A1 | 10/2016 | Girgenti | |
| 2017/0079720 A1 | 3/2017 | Velusamy | |
| 2018/0256279 A1 | 9/2018 | Girgenti | |
| 2022/0257331 A1 | 8/2022 | Girgenti | |

FOREIGN PATENT DOCUMENTS

| | | |
|---|---|---|
| WO | 0028882 | 5/2000 |
| WO | 02/41794 | 5/2002 |
| WO | 021794 | 5/2002 |
| WO | 2010113633 | 10/2010 |
| WO | 2013040017 | 3/2013 |
| WO | 2014081908 | 5/2014 |

OTHER PUBLICATIONS

European Communication in Application 12832632.9, mailed Jan. 2, 2018, 5 pages.

European Communication in Application 12832632.9, mailed Feb. 26, 2019, 5 pages.

European Search Report dated Jun. 28, 2016, in European Patent Application No. 13856085.9.

European Supplementary Search Report dated Feb. 5, 2015, in corresponding European Patent Application No. EP 12 83 2632.

PCT International Preliminary Report on Patentability dated Mar. 18, 2014, from corresponding PCT Application No. PCT/US12/54835.

PCT International Search Report dated Nov. 29, 2012 PCT/US12/54835 pp. 1-9.

(56) References Cited

OTHER PUBLICATIONS

PCT Interntional Preliminary Report on Patentability in International Application PCT/US2013/071139, mailed Jun. 4, 2015, 6 pages.

PCT Interntional Search Report and Written Opinion in International Application PCT/US2013/071139, mailed Apr. 14, 2014, 12 pages.

* cited by examiner

SECTION K-K

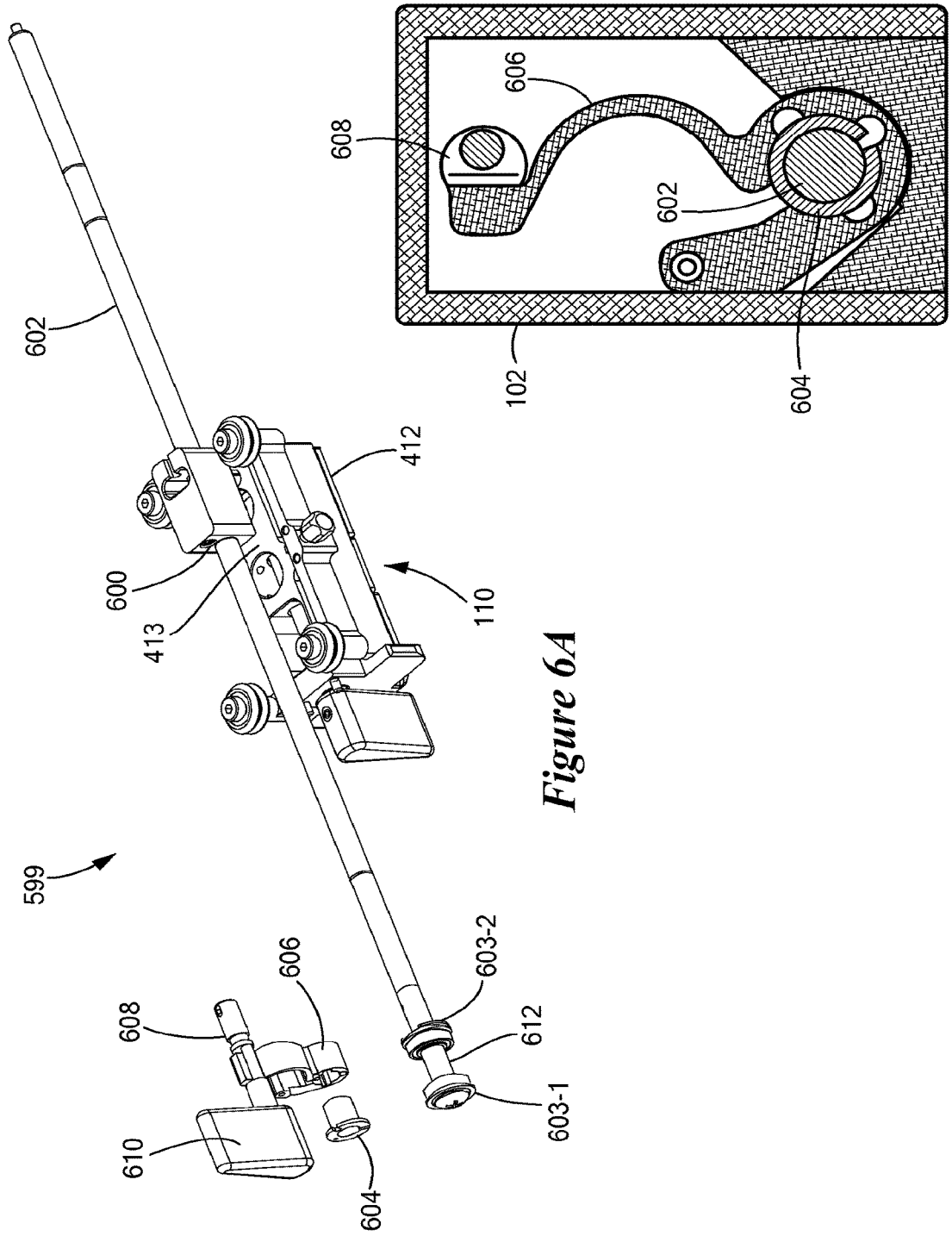

SECTION B1-B1

SECTION B1.1-B1.1

SECTION B2-B2

SECTION C1-C1

SECTION C2-C2

BREAST BIOPSY LATERAL ARM SYSTEM

CROSS-REFERENCE TO RELATED APPLICATIONS

This application is a continuation application of U.S. patent application Ser. No. 14/646,630 (now U.S. Pat. No. 11,284,869), filed May 21, 2015, which application is a National Stage Application of PCT/US2013/071139, filed Nov. 21, 2013, which claims priority to and the benefit of U.S. Provisional Patent Application Ser. No. 61/729,141, filed Nov. 21, 2012, and is also a continuation-in-part of U.S. patent application Ser. No. 13/611,502 (now U.S. Pat. No. 9,308,017), filed on Sep. 12, 2021, which application claims priority to and the benefit of U.S. Provisional Patent Application Ser. No. 61/535,401, filed Sep. 16, 2011, the entire disclosures of which are hereby incorporated herein by reference.

BACKGROUND

The subject matter of this application is generally related to the medical field. Medical imaging technologies such as stereotactic x-ray, fluoroscopy, computer tomography, ultrasound, nuclear medicine and magnetic resonance imaging enable detection of small abnormalities in the body of a patient. The discovery of certain abnormalities may prompt performance of a biopsy procedure to obtain a tissue sample for lab analysis to help diagnose and treat patients suspected of having cancerous tumors, pre-malignant conditions or other diseases or disorders. A stereotactic guided percutaneous breast biopsy is often preferable to an open surgical breast biopsy in the case of small abnormalities located deep within the body because a percutaneous biopsy removes a relatively small amount of tissue. For example, a needle can be used to remove individual cells or clusters of cells in the case of fine needle aspiration (FNA), and a core or fragment of tissue in the case of a core biopsy. One difficulty associated with such procedures is that it is necessary to locate the biopsy needle with considerable precision in order to obtain a suitable sample of a small abnormality, particularly if it is located deep within the body. Moreover, it would be advantageous if the medical equipment for performing such procedures were practical to manufacture at a reasonable cost and usable by medical personnel without extensive training.

SUMMARY

In accordance with an aspect, an apparatus comprises: a lateral arm; a carriage assembly which traverses along the lateral arm in a predefined axis, the carriage assembly including a carriage and self-adjusting rollers which are loaded against the lateral arm by spring members; and a gun mount configured to support a biopsy gun, the gun mount being connected to the carriage. The self-adjusting rollers may include a set of fixed guide rollers on a first side of the lateral arm and a movable set of guide rollers on a second side of the lateral arm. One or more spring members may be used to load the movable set of guide rollers against the lateral arm. The spring member may include a resilient beam. A cam-actuated X-axis stop may be removably secured to the lateral arm to limit an extent of traverse of the carriage.

In accordance with another aspect, an apparatus comprises: a lateral arm; a carriage which traverses along the lateral arm in a predefined axis; a cam-actuated lock assembly which secures the carriage to the lateral arm in an engaged state; and a gun mount configured to support a biopsy gun, the gun mount being connected to the carriage. Movement of the carriage relative to the lateral arm may be controlled by a lead screw associated with the lateral arm and carriage nut attached to the carriage, and the lock assembly may include a clamp which applies frictional force to the lead screw in response to actuation of a camshaft, thereby inhibiting rotation of the lead screw. A clamp bushing may be disposed between the clamp and the lead screw. A cam-actuated X-axis stop may be removably secured to the lateral arm to limit an extent of traverse of the carriage.

In accordance with another aspect, an apparatus comprises: a lateral arm; a carriage which traverses along the lateral member in a predefined axis; a gun mount configured to support a biopsy gun, the gun mount being connected to the carriage; and a cam-actuated locking mechanism for securing the gun mount to the carriage. A positional offset feature may be provided which repositions the gun mount along a secondary axis which is orthogonal to the predefined axis. The locking mechanism may include a tee nut associated with the carriage and a corresponding tee slot associated with the gun mount. A camshaft can be used to actuate the tee nut to apply frictional force against the tee slot in an engaged state. The camshaft may actuate the tee nut in the engaged state by allowing a spring to apply force directly to the tee nut, such that the camshaft does not apply force against the tee slot via the tee nut. A camshaft may actuate a locking pilot pin associated with the carriage, the pin applying force against the gun mount. The camshaft may actuate the locking pilot pin in an engaged state by allowing a spring to apply force directly to the locking pilot pin, such that the camshaft does not apply force against the gun mount via the locking pilot pin. The carriage may include at least one stop pin and the gun mount may include at least one stop pin seat, such that the gun mount is aligned in a predetermined relationship with the carriage when the stop pin is fully inserted into the stop pin seat. First and second sets of stop pin seats may be provided such that the first set of stop pin seats align the gun mount in a position offset by 180 degrees from an alignment position determined by the second set of stop pin seats.

In accordance with another aspect, a method comprises: securing a biopsy needle to a gun mount associated with a carriage; and positioning the biopsy needle for a procedure by traversing the carriage along a lateral arm in a predefined axis, including the carriage riding on self-adjusting rollers which arc loaded against the lateral arm by spring members. The self-adjusting rollers may include a set of fixed guide rollers on a first side of the lateral arm and a movable set of guide rollers on a second side of the lateral arm. At least one spring member may be used to load the movable set of guide rollers against the lateral arm. The spring member may include a resilient beam. A cam-actuated X-axis stop may be secured to the lateral arm to limit an extent of traverse of the carriage.

In accordance with another aspect, a method comprises: securing a biopsy needle to a gun mount associated with a carriage; and positioning the biopsy needle for a procedure by traversing the carriage along the lateral arm in a predefined axis; and securing the carriage to the lateral arm via a cam-actuated lock assembly. Movement of the carriage relative to the lateral arm may be controlled by a lead screw associated with the lateral arm and carriage nut attached to the carriage, and the lock assembly may include a clamp which applies frictional force to the lead screw in response to actuation of a camshaft, thereby inhibiting rotation of the lead screw. A clamp bushing may be disposed between the clamp and the lead screw. A cam-actuated X-axis stop may be secured to the lateral arm to limit an extent of traverse of the carriage.

In accordance with another aspect, a method comprises: securing a biopsy needle to a gun mount via a cam-actuated locking mechanism, the gun mount associated with a carriage; and positioning the biopsy needle for a procedure by traversing the carriage along the lateral arm in a predefined axis. A positional offset feature may be provided to reposition the gun mount along a secondary axis which is orthogonal to the predefined axis. The locking mechanism may include a tee nut associated with the carriage and a corresponding tee slot associated with the gun mount. A camshaft can be used to actuate the tee nut to apply frictional force against the tee slot in an engaged state. For example, the camshaft may actuate the tee nut in the engaged state by allowing a spring to apply force directly to the tee nut, such that the camshaft does not apply force against the tee slot via the tee nut. A camshaft can be used to actuate a locking pilot pin associated with the carriage, the pilot pin applying force against the gun mount. The camshaft may actuate the locking pilot pin in an engaged state by allowing a spring to apply force directly to the locking pilot pin, such that the camshaft does not apply force against the gun mount via the locking pilot pin. The carriage may include at least one stop pin and the gun mount may include at least one stop pin seat, such that the gun mount is aligned in a predetermined relationship with the carriage when the stop pin is fully inserted into the stop pin scat. First and second sets of stop pin seats may be provided such that the first set of stop pin seats align the gun mount in a position offset by 180 degrees from an alignment position determined by the second set of stop pin seats.

Unless specifically stated otherwise, the features described herein can be used in any combination, and the aspects can include any one or more of the embodiments. Moreover, other features and advantages will become apparent to those of ordinary skill in the art in view of the figures and detailed description.

BRIEF DESCRIPTION OF THE FIGURES

FIG. 6A is a partly exploded perspective view of the combination of the carriage slide locking assembly and the carriage assembly shown in FIG. 5B;

FIG. 6B is a section view taken along line P-P of FIG. 5A;

DETAILED DESCRIPTION

Figure 1:
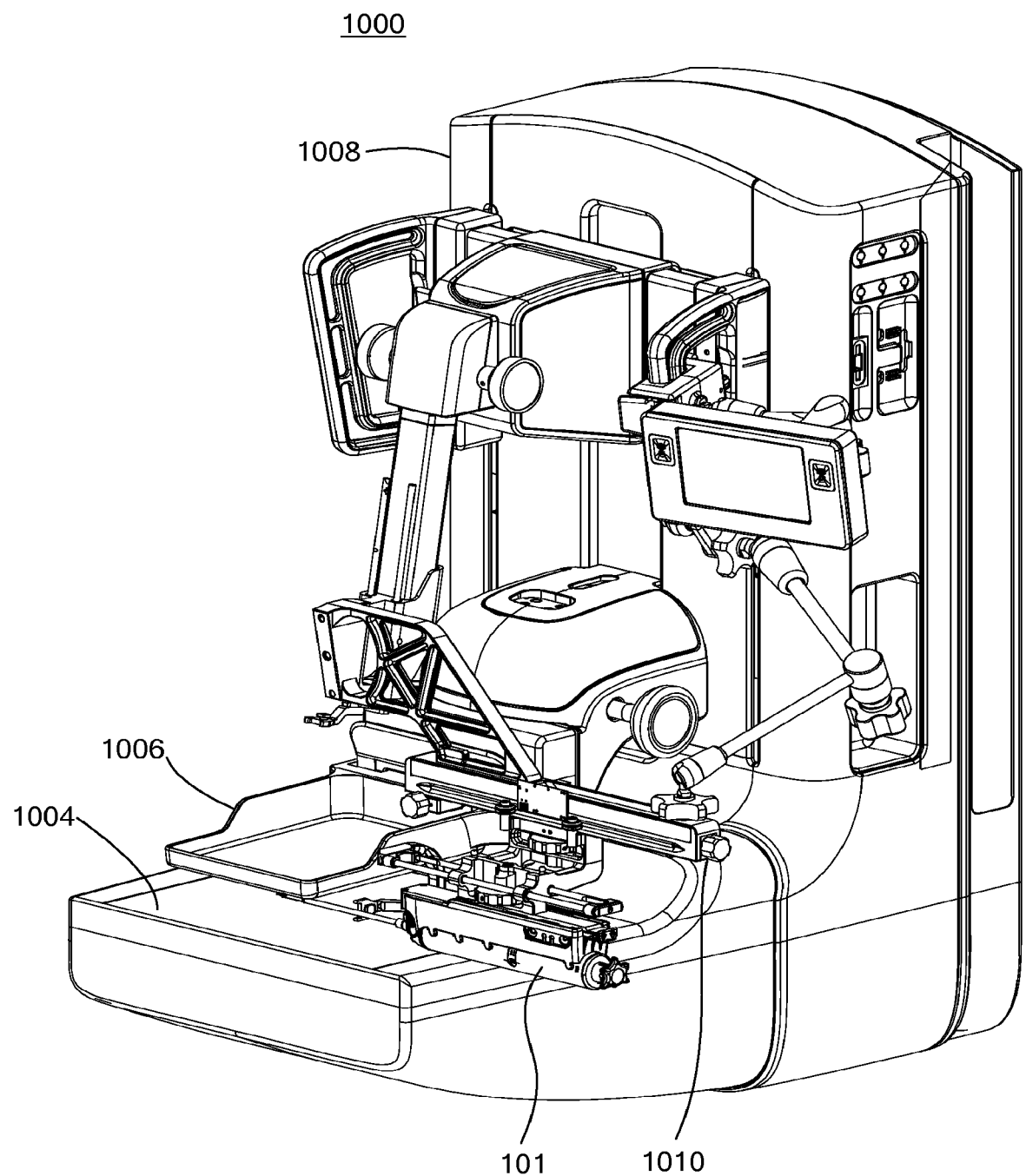
FIGS. 1 and 2 are isometric and side views, respectively, of one embodiment of a breast biopsy station according to the present invention, the breast biopsy station being shown in FIG. 2 together with a breast.
Figure 2:
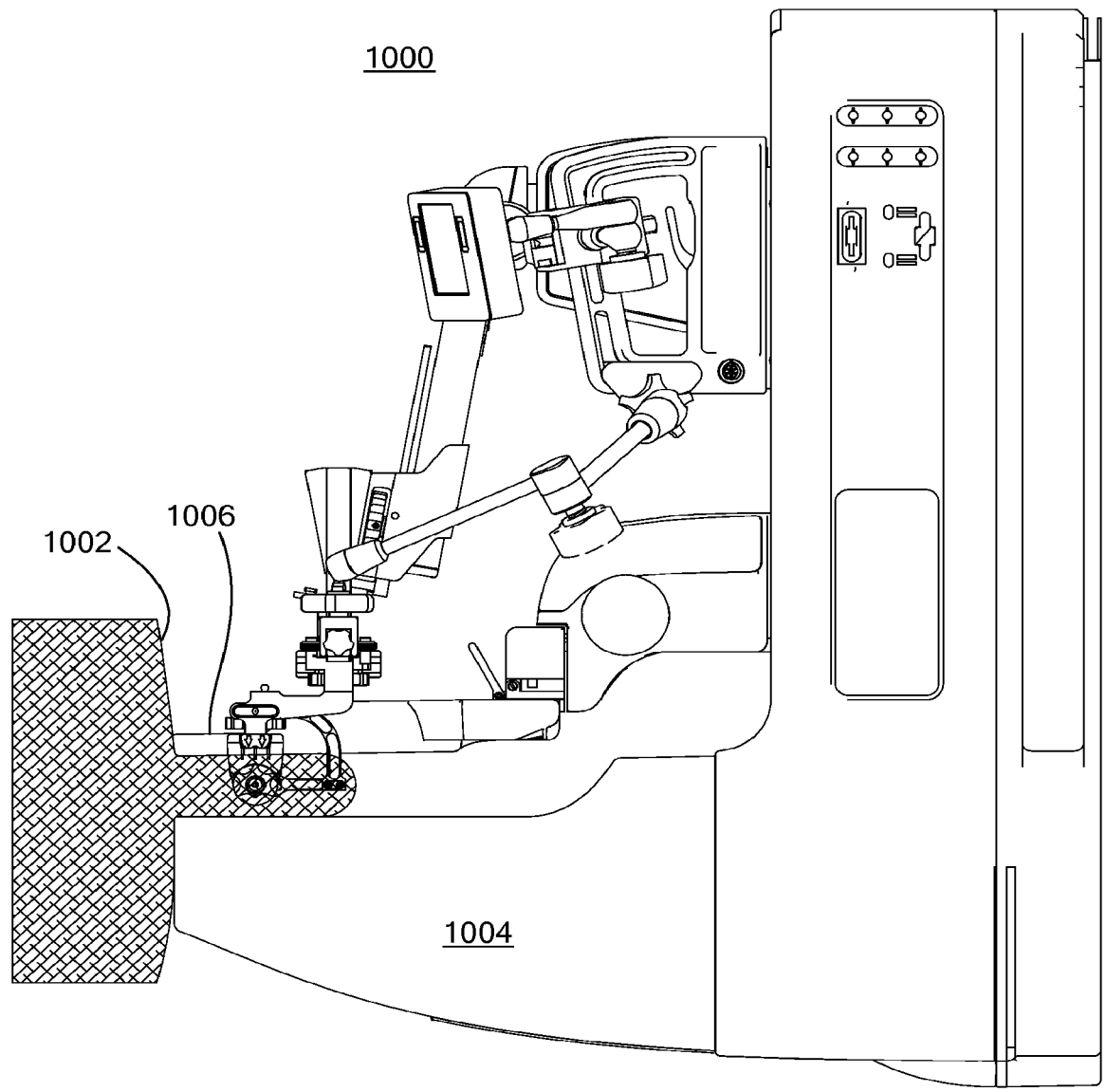

Referring to FIGS. 1 and 2, there is shown one embodiment of a breast biopsy station according to the present invention, the breast biopsy station being represented generally by reference numeral 1000. Breast biopsy station 1000 may comprise a breast platform 1004, a compression paddle 1006, a radiographic imaging system 1008, and an integrated biopsy needle guidance system 1010. As seen best in FIG. 2, breast platform 1004 and compression paddle 1006 may be arranged so that the chest wall 1002 of a patient may be pressed against breast platform 1004 and compression paddle 1006, with the patient's breast being positioned on top of breast platform 1004 and under compression paddle 1006, i.e., the breast may be compressed between breast platform 1004 and compression paddle 1006. Radiographic imaging system 1008 may be used to produce an image of the breast that is compressed between breast platform 1004 and compression paddle 1006 in order to locate a feature of interest, e.g., a lesion, located within the breast. Integrated biopsy needle guidance system 1010 may be used to obtain a tissue sample of the feature of interest. More particularly, integrated biopsy needle guidance system 1010 may display information about the relative locations of the targeted feature and a biopsy gun 101 in order to help position biopsy gun 101 and to guide its path of travel such that a needle on biopsy gun 101 may intersect with the target feature.

Figure 3:
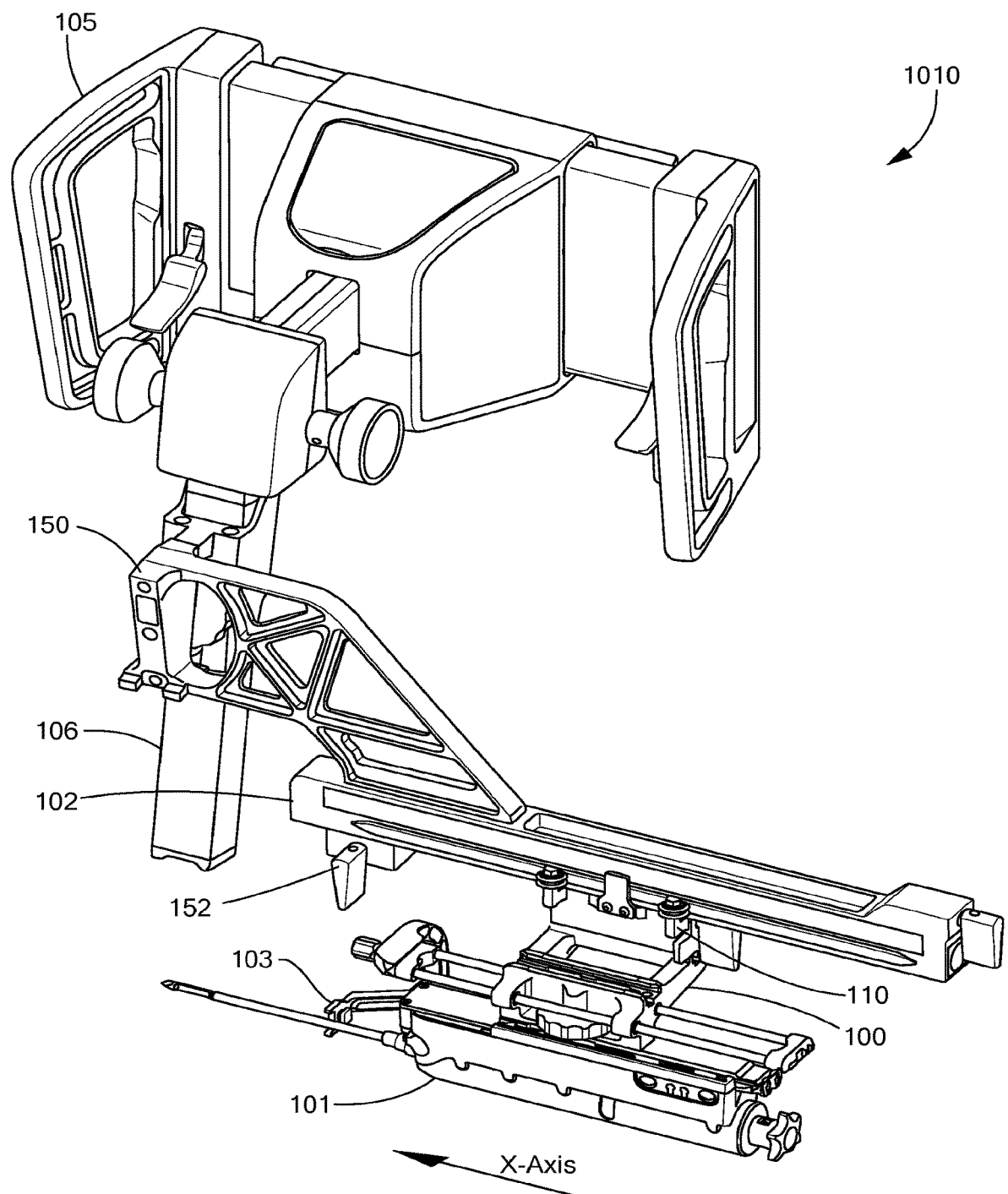
FIG. 3 is an isometric view of the integrated biopsy needle guidance system of the breast biopsy station of FIG. 1.

Referring now to FIG. 3, there is shown integrated biopsy needle guidance system 1010 in greater detail. Integrated biopsy needle guidance system 1010 may comprise a gun mount 100, a carriage assembly 110, a lateral arm 102, and a biopsy guidance module 105. Biopsy gun 101 may be connected to gun mount 100. Gun mount 100 may be connected to carriage assembly 110. Carriage assembly 110 may be connected to lateral arm 102. Lateral arm 102 may be connected to biopsy guidance module 105. Biopsy guidance module 105 may include interface features which help calculate, utilize and display useful information. Reconfiguration features may be provided to allow secure repositioning of the selected biopsy gun, and sensing features such as described in U.S. patent application Ser. No. 13/611,502, inventors Girgenti et al., filed Sep. 12, 2012, titled Breast Biopsy Lateral Arm System, which is incorporated herein by reference in its entirety, may be provided to detect certain reconfiguration and repositioning data in order to facilitate the biopsy procedure, e.g., by providing the data to the biopsy guidance module in order to automate calculation of offsets, adjustments and other information that helps to obtain tissue cores from a specific location. Moreover, the data can be used to verify that a configuration entered by an operator matches the actual configuration of the needle guidance system.

A selected biopsy gun 101 may be positioned and secured by gun mount 100. More particularly, an operator can securely mount and remove any of various biopsy guns that might be selected, so different biopsy guns may be utilized as needed. Indexing features may help assure that the biopsy gun can be predictably and repeatedly mounted in a particular position with respect to the gun mount when mounted. Biopsy gun 101 may be operative in response to information from an embedded computer, information provided by an operator via biopsy guidance module 105, and sensor input to locate a biopsy needle of biopsy gun 101 to obtain a tissue sample, e.g., by inserting an outer cannula into a predetermined location of interest within the patient, extracting a tissue core sample by moving an inner cannula relative to the outer cannula, and removing the needle from the patient. A needle guide 103 may help to guide the outer cannula of the biopsy gun, e.g., by inhibiting deflection. Various types of biopsy guns and needles are known, and the functioning of biopsy guns and needles in obtaining tissue cores is well understood in the art. Therefore, these features will not be described in greater detail.

One aspect of positioning biopsy gun 101 relative to the patient may be via movement of lateral arm 102. Biopsy guidance module 105 may include a post member 106. Lateral arm 102 may include a clamp member 150 which can be slidably moved along and secured to post member 106 at any of various locations along the length of post member 106. As a result, biopsy gun 101 may be repositionable via movement of lateral arm 102 with respect to post member 106.

Another aspect of positioning the biopsy gun 101 relative to the patient may be via movement of biopsy gun 101 relative to lateral arm 102. Carriage assembly 110 may be selectively movable (e.g., slidably) along an X-axis defined by lateral arm 102, to which carriage assembly 110 may be connected. When biopsy gun 101 is secured to gun mount 100, and gun mount 100 is secured to carriage assembly 110, biopsy gun 101 may be positioned at any of various points along the X-axis by moving carriage assembly 110 with respect to lateral arm 102. A carriage slide locking feature may enable an operator to secure carriage assembly 110 to lateral arm 102 when a desired X-axis position is attained, thereby securing biopsy gun 101 in a desired X-axis position relative to the patient. Moreover, an X-axis stop 152 may be used to reliably return biopsy gun 101 to a particular X-axis position.

Figure 4:
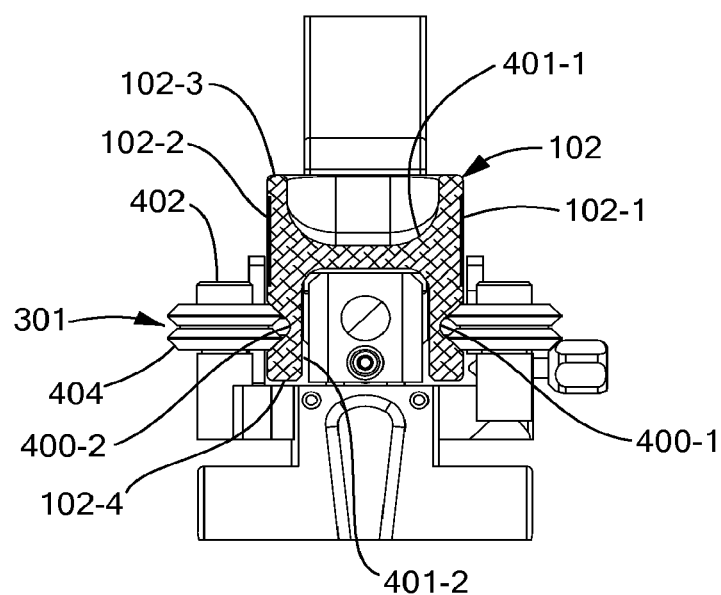
FIG. 4 is a cross-sectional view taken along line K-K of FIG. 5A, illustrating the roller guide wheels of the carriage assembly and the generally V-shaped grooves of the lateral arm of the needle guide system in greater detail.
Figure 5A:
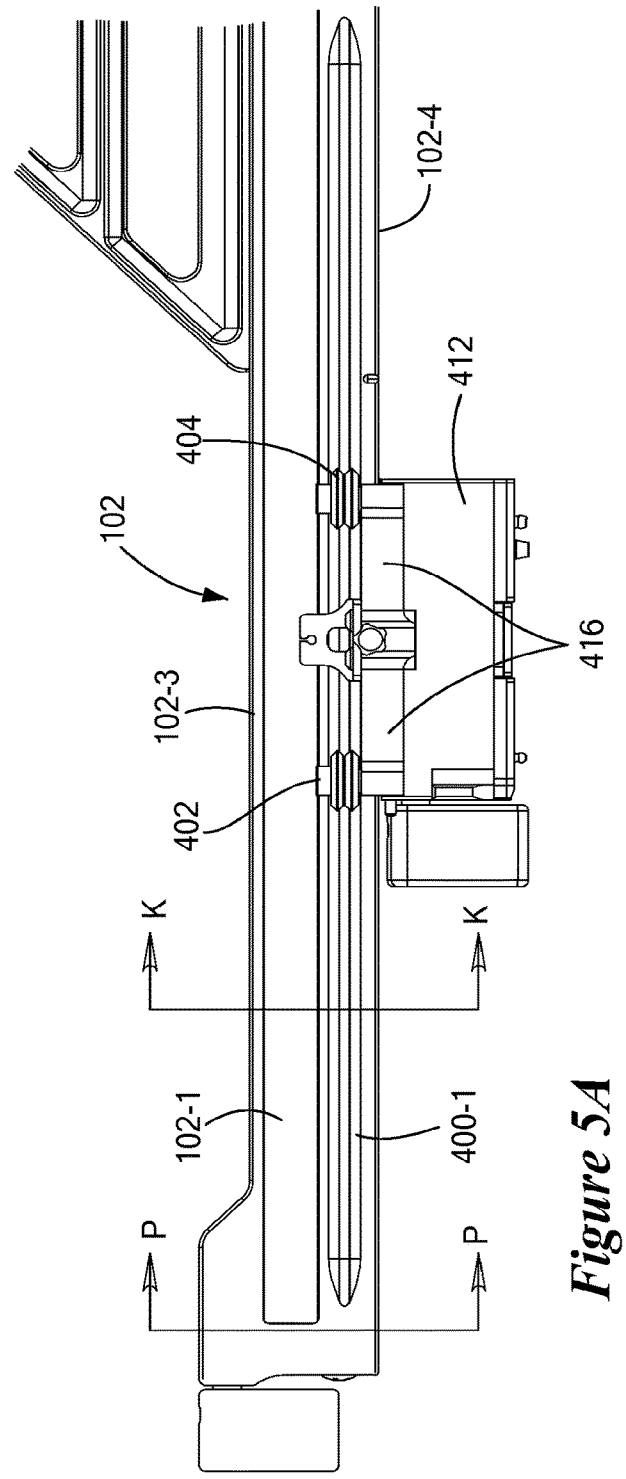
FIG. 5A is a side view of certain components of the integrated biopsy needle guidance system shown in FIG. 3.
Figure 5B:
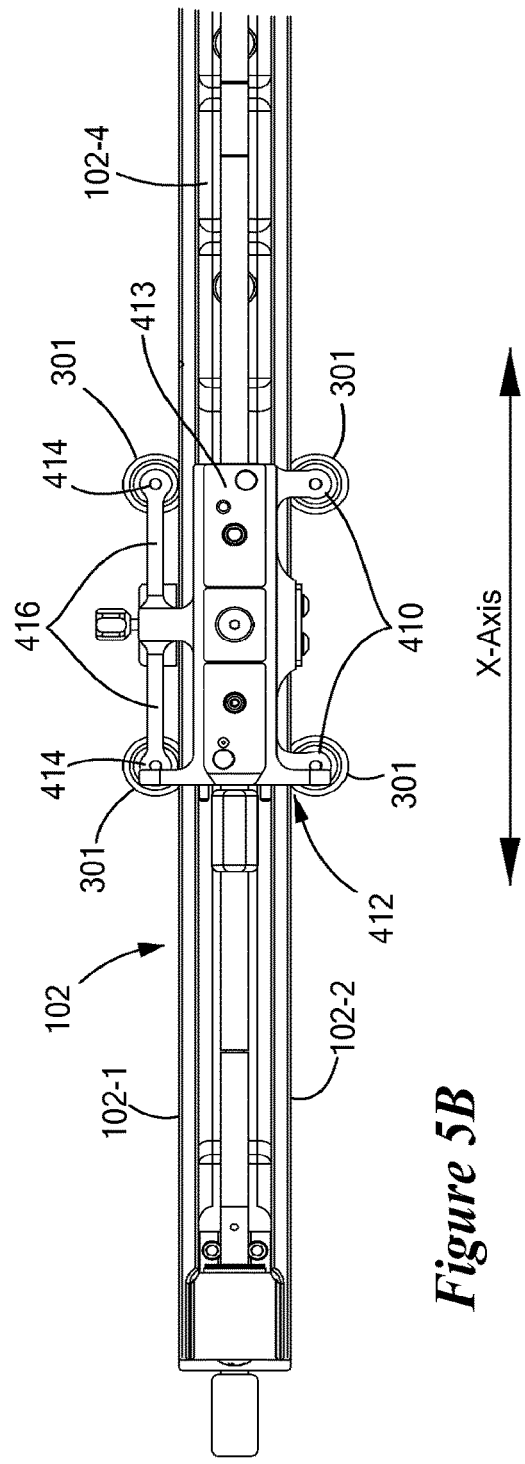
FIG. 5B is a bottom view of certain components of the integrated biopsy needle guidance system shown in FIG. 3.

Referring now to FIGS. 4, 5A and 5B, lateral arm 102 may comprise an elongated member that may be generally H-shaped in transverse cross-section. Lateral arm 102 may be shaped to include a first side surface 102-1, a second side surface 102-2, a top surface 102-3, and a bottom surface 102-4. A first generally V-shaped groove 400-1 with a rounded vertex may be provided in first side surface 102-1 of lateral arm 102, and a second generally V-shaped groove 400-2 with a rounded vertex may be provided in second side surface 102-2 of lateral arm 102. First and second generally V-shaped grooves 400-1 and 400-2 may extend for at least a portion of the length of lateral arm 102, with first and second generally V-shaped grooves 400-1 and 400-2 extending parallel to one another along the X-axis of lateral arm 102. A top channel 401-1 may be provided in top surface 102-3 of lateral arm 102, and a bottom channel 401-2, the purpose of which will become apparent below, may be provided in bottom surface 102-4 of lateral arm 102.

Carriage assembly 110 may comprise a carriage 412. Carriage 412, in turn, may comprise a structure, optionally a unitary structure, shaped to include a central body 413, a set of fixed guide roller mounts 410 positioned on a first side of central body 413, and a set of self-adjusting guide roller mounts 414 positioned on a second side of central body 413. As will be discussed further below, fixed guide roller mounts 410 and self-adjusting guide roller mounts 414 may be used to mount guide rollers 301 that, in turn, may engage lateral arm 102 by seating against generally V-shaped grooves 400-1 and 400-2. More specifically, self-adjusting guide roller mounts 414 may be positioned proximate to first side surface 102-1 of lateral arm 102, with its associated guide rollers 301 seated against generally V-shaped groove 400-1, and fixed guide roller mounts 410 may be positioned proximate to second side surface 102-2 of lateral arm 102, with its associated guide rollers 301 seated against generally V-shaped groove 400-2. Self-adjusting guide roller mounts 414 may be connected to one another by deflecting beams 416. Deflecting beams 416 may allow self-adjusting guide roller mounts 414 to flex laterally relative to central body 413 whereas fixed guide roller mounts 410 may not move relative to central body 413. Deflecting beams 416 may be resilient and/or may serve to apply a spring force to help keep guide rollers 301 seated against generally V-shaped grooves 400-1 and 400-2, thereby compensating for dimensional variations associated with the machining processes of related parts. Deflecting beams 416 may be formed by machining carriage 412 in a manner that leaves two thin beams of aluminum or other suitable material which are designed to deflect to a pre-determined position and apply a pre-determined force when deflected. The deflection creates a preload force that helps keep guide rollers 301 engaged against generally V-shaped grooves 400-1 and 400-2. However, a wide variety of means of applying spring force might also be utilized.

As noted above, guide rollers 301 may allow carriage 412 to travel along the X-axis of lateral arm 102 while inhibiting movement of carriage 412 outside the X-axis. Each guide roller 301 may include a bearing 402 and a wheel 404.

Wheel 404 may be appropriately shaped to contact its respective generally V-shaped groove 400-1 or 400-2 and to center guide roller 301 therewithin. Wheel 404 may be shaped to include a central groove, which may be generally V-shaped, generally U-shaped, or any other of a wide variety of shapes. The outer edges of wheel 404 may be chamfered so that contact with generally V-shaped groove 400-1 or 400-2 does not prevent wheel 404 from centering within the generally V-shaped groove. Wheel 404 may be connected to carriage 412 via bearing 402, which may enable wheel 404 to turn as carriage assembly 110 is moved along the X-axis of lateral arm 102.

Referring now to FIG. 6A, there is shown the combination of a carriage slide locking assembly 599 and carriage assembly 110. As will become apparent from the discussion below, carriage slide locking assembly 599 may be constructed so that, when in an unlocked state, carriage locking assembly 599 allows carriage assembly 110 to move freely along the x-axis of lateral arm 102, and so that, when in a locked state, carriage locking assembly 599 secures carriage assembly 110 to lateral arm 102 at a desired position along the x-axis of lateral arm 102. Carriage locking assembly 599 may comprise a carriage nut 600, a lead screw 602, lead screw bearings 603-1 and 603-2, a clamp bushing 604, a clamp 606, a camshaft 608, and a carriage locking knob 610. Carriage nut 600 may be fixed to the top of central body 413 of carriage 412 and may be appropriately dimensioned to slide longitudinally back and forth within channel 401-2 of lateral arm 102. Lead screw 602 may be coupled to lateral arm 102 via lead screw bearings 603-1 and 603-2 in such a way that lead screw 602 may rotate about its longitudinal axis while otherwise being fixed to lateral arm 102. Lead screw 602 may extend through a longitudinal bore in carriage nut 600. Carriage nut 600 and lead screw 602 may have complementary internal and external threads (not shown) so that, as lead screw 602 is rotated, carriage nut 600 is caused to move along the x-axis of lead screw 602, the direction of X-axis movement being a function of the direction of rotation of lead screw 602.

Once carriage nut 600 has been positioned at a desired location along the x-axis of lead screw 602, further rotation of lead screw 602 may be limited by the combination of clamp bushing 604, clamp 606, camshaft 608, and carriage locking knob 610. More specifically, clamp bushing 604 may be positioned coaxially around an unthreaded clamping portion 612 of lead screw 602 that is located between lead screw bearings 603-1 and 603-2. One end of clamp 606 may be positioned proximate to clamp bushing 604, and the opposite end of clamp 606 may be coupled to camshaft 608. Camshaft 608, which may be mechanically coupled to and actuated by rotation of carriage locking knob 610, may include a machined section which may be asymmetrical with respect to the axis about which camshaft 608 rotates. In the unlocked state, camshaft 608 does not apply any force to clamp 606 due to the asymmetry of the machined section. As a result, clamp 606 does not cause clamp bushing 604 to grip lead screw 602 at clamping surface 612; consequently, lead screw 602 is free to rotate, and carriage assembly 110 may move along the x-axis of lateral arm 102. By contrast, in the locked state (see FIG. 6B), the asymmetrical cam section on camshaft 608 bears down on clamp 606, causing clamp 606 to compress clamp bushing 604 against lead screw 602, thereby preventing lead screw 602 from rotating due to frictional force between bushing 604 and clamping surface 612. Such a lack of rotation of lead screw 602 keeps carriage nut 600 from moving and, thereby, prevents carriage assembly 110 from moving along the x-axis of lateral arm 102.

Figure 7C:
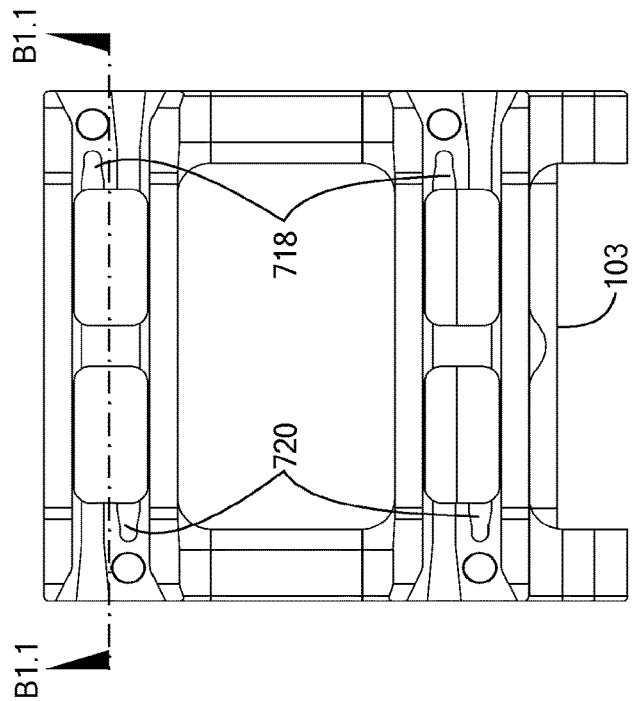
FIG. 7C is a top view of the gun mount shown in FIG. 7A, together with the needle guide.
Figure 7A:
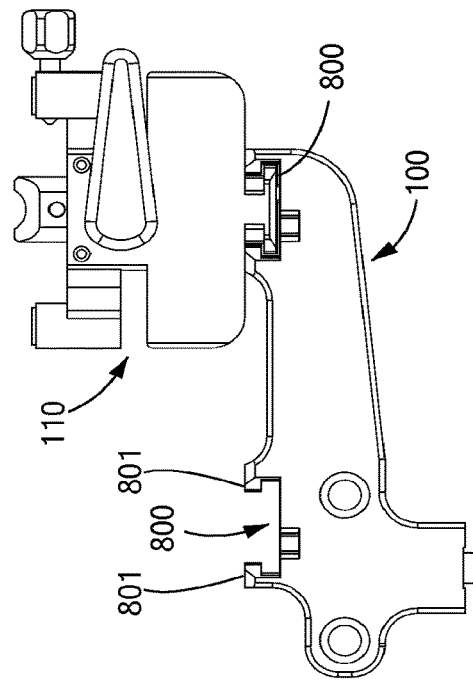
FIG. 7A is an end view of the combination of the gun mount and the carriage assembly of FIG. 3, the roller guide wheels of the carriage assembly not being shown, the locking knob of the carriage assembly being shown in an unlocked or disengaged position.
Figure 7B:
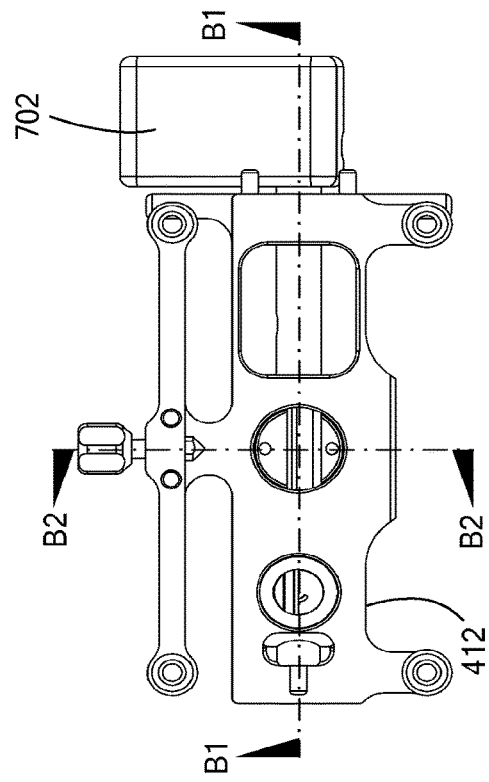
FIG. 7B is a top view of the carriage assembly of FIG. 7A, the roller guide wheels of the carriage assembly not being shown, the locking knob of the carriage assembly being shown in an unlocked or disengaged position.

Referring now to FIGS. 7A through 7F and to FIGS. 8A through 8D, the manner in which carriage assembly 110 and gun mount 100 may be reversibly and lockably interconnected is made apparent. In particular, FIG. 7A shows carriage assembly 110 and gun mount 100 interconnected in an unlocked state, and FIGS. 8A through 8D show carriage assembly 110 and gun mount 100 interconnected in a locked state.

Figure 7D:
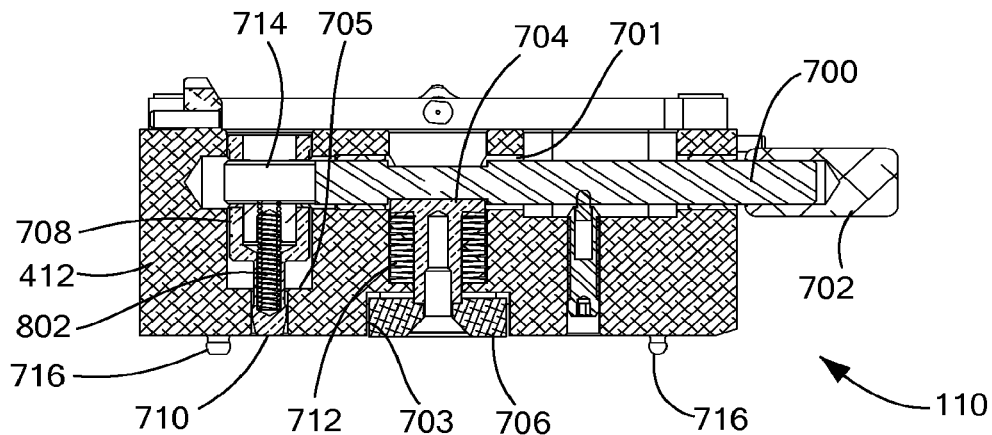
FIGS. 7D and 7E are cross-sectional views corresponding to FIGS. 7B and 7C, respectively, taken along section lines B1-B1 and B1.1-1.1.
Figure 7E:
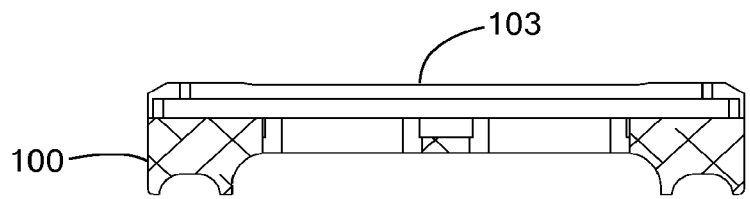
Figure 7F:
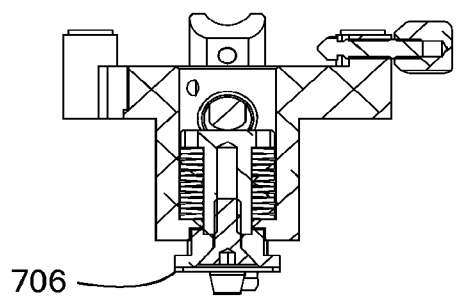
FIG. 7F is a cross-sectional view of the carriage assembly of FIG. 7B taken along section line B2-B2.
Figure 8A:
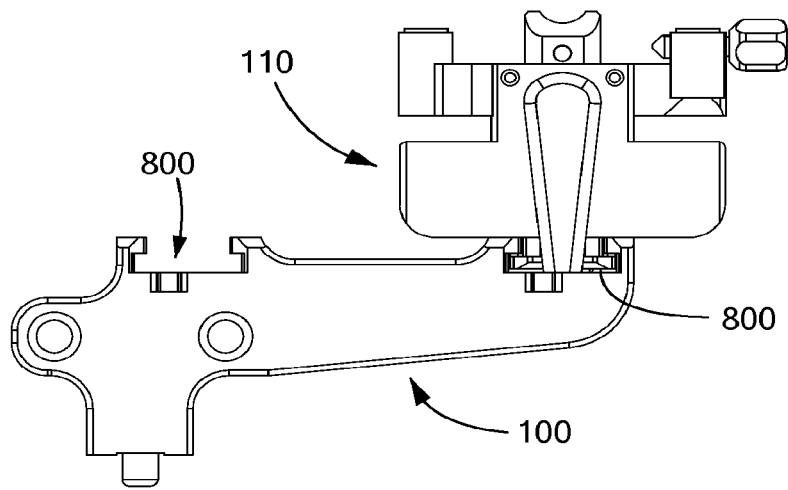
FIG. 8A is an end view of the combination of the gun mount and the carriage assembly of FIG. 3, the roller guide wheels of the carriage assembly not being shown, the locking knob of the carriage assembly being shown in a locked or engaged position.
Figure 8B:
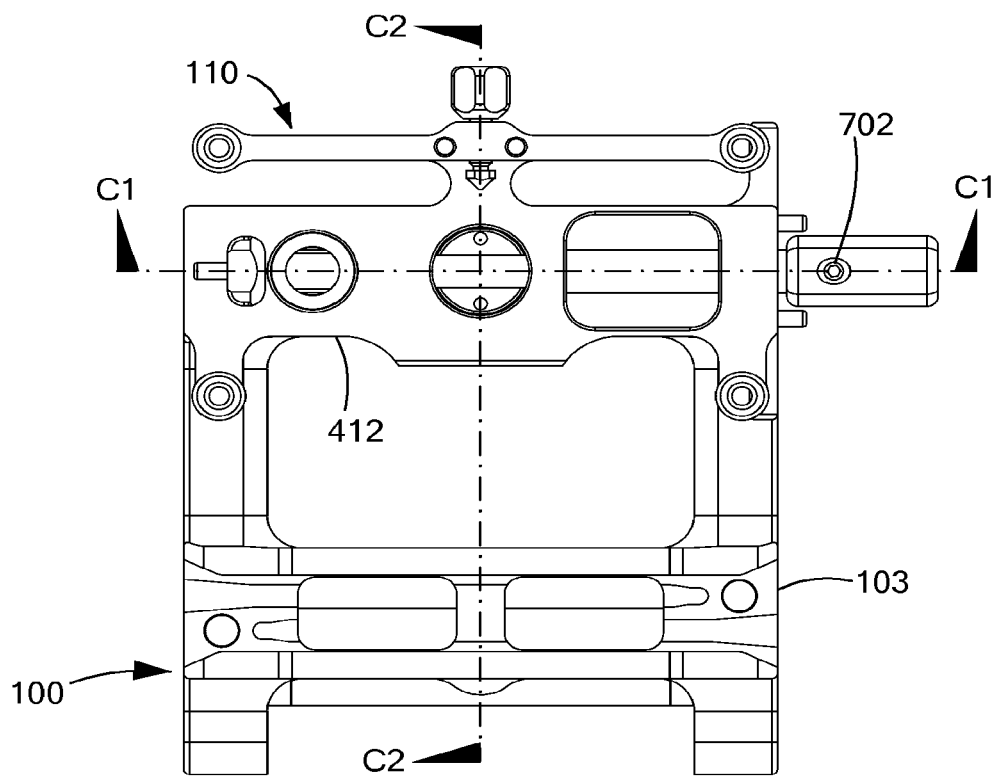
FIG. 8B is a top view of the combination of the gun mount and the carriage assembly shown in FIG. 8A.
Figure 8C:
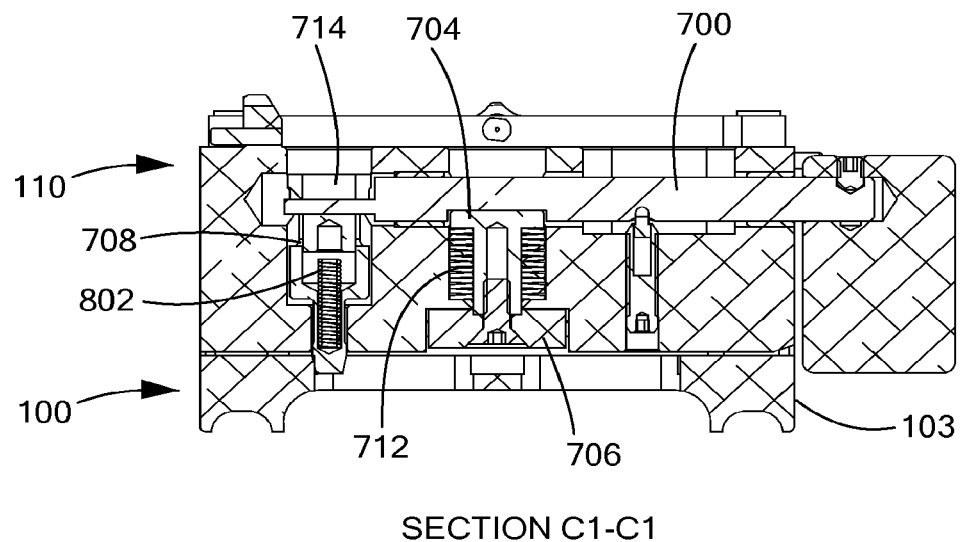
FIG. 8C is a cross-sectional view of the combination of the gun mount and the carriage assembly shown in FIG. 8B taken along section line C1-C1.
Figure 8D:
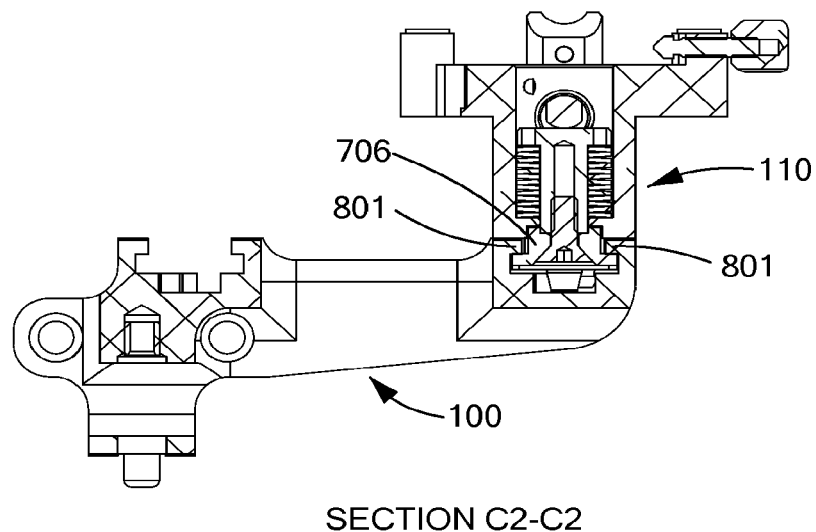
FIG. 8D is a cross-sectional view of the combination of the gun mount and the carriage assembly shown in FIG. 8B taken along line section C2-C2.
Figure 9:
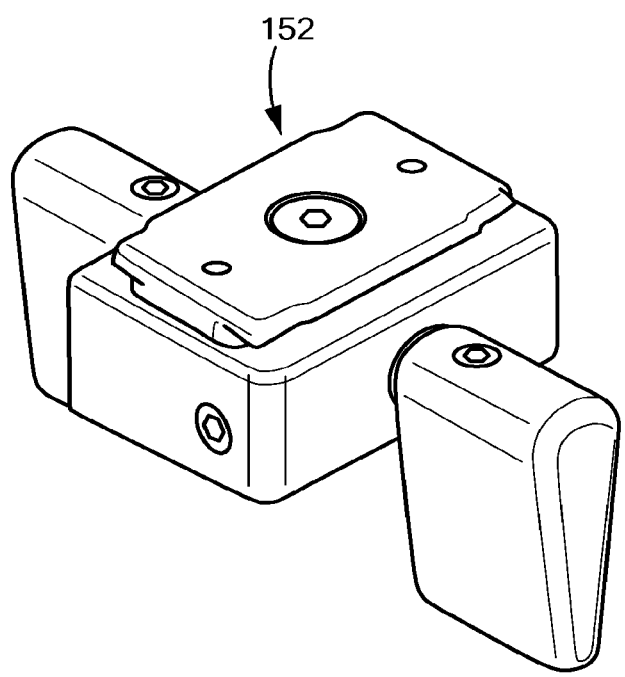
FIG. 9 is an isometric view of the X-axis stop shown in FIG. 3.

As can be seen, for example, in FIG. 7D, carriage assembly 110 may further comprise a camshaft 700. Camshaft 700 may be rotatably mounted within a cavity 701 that may be provided in carriage 412. A locking knob 702, which may be disposed outside of carriage 412, may be mechanically coupled to camshaft 700 and may be used to rotate camshaft 700. Carriage assembly 110 may further comprise a tee nut 706. Tee nut 706 may be movably mounted in a vertical direction relative to a cavity 703 that may be provided in carriage 412. Vertical movement of tee nut 706 relative to cavity 703 may be controlled by camshaft 700, a tee nut cam follower 704, and tee nut springs 712. More specifically, camshaft 700 and tee nut cam follower 704 may be sized and shaped so that, when camshaft 700 is in an unlocked or disengaged position (i.e., locking knob 702 horizontal), camshaft 700 causes tee nut cam follower 704 to cause tee nut springs 712 to be compressed, thereby lowering tee nut 706 to its lowest operating position (see, for example, FIG. 7F). By contrast, when camshaft 700 is in a locked or engaged position (i.e., locking knob 702 vertical), camshaft 700 causes tee nut cam follower 704 to cause tee nut springs 712 not to be compressed, thereby raising tee nut 706 to its highest operating position (see, for example, FIG. 8C).

Carriage assembly 110 may further comprise a locking pilot pin 710. Locking pilot pin 710 may be movably mounted in a vertical direction into and partially out of a cavity 705 that may be provided in carriage 412. Vertical movement of locking pilot pin 710 may be controlled by a secondary cam 714 on camshaft 700, a secondary lock cam follower 708, and a secondary lock spring 802. More specifically, secondary cam 714 and secondary lock cam follower 708 may be sized and shaped so that, when camshaft 700 is an unlocked or disengaged position (i.e., locking knob 702 horizontal), locking pilot pin 710 is raised to a position that is entirely within cavity 705 (see, for example, FIG. 7D). By contrast, when camshaft 700 is in a locked or engaged position (i.e., locking knob 702 vertical), locking pilot pin 710 is driven down to a position that extends partially out of cavity 705 (see, for example, FIG. 8C).

Carriage assembly 110 may further comprise one or more X-axis stop pins 716 fixedly mounted on the bottom of carriage 412. X-axis stop pins 716 may be used to mate with X-axis stop pin seats 718 provided in gun mount 100 in such a way that gun mount 100 may be properly aligned with carriage 412 only when stop pins 716 are disposed in stop pin seats 718. Such positioning facilitates calculations associated with biopsy needle positioning relative to the patient. An additional set of X-axis stop pin seats 720 may be provided in gun mount 100 to allow gun mount 100 to be mounted in a 180 degree offset position.

To couple gun mount 100 to carriage assembly 110, locking knob 702 may be placed in a horizontal position (toward either side). Placement of locking knob 702 in such a horizontal position orients camshaft 700 so that tee nut cam follower 704 compresses tee nut springs 712, thereby lowering tee nut 706 to its lowest operating position. In addition, placement of locking knob 702 in such a horizontal position also causes locking pilot pin 710 to be raised into cavity 705 of carriage 412. With tee nut 706 thus lowered and locking pilot pin 710 thus raised, carriage assembly 110 may then be coupled to gun mount by sliding the bottom end of carriage 412, as well as tee nut 706, into one of the two tee slots 800 provided in gun mount 100 until stop pins 716 are seated within their corresponding stop pin seats 718. Locking knob 702 may then be turned to its vertical position (i.e., an approximately 90 degree rotation) in order to lock gun mount 100 to carriage assembly 110. The rotation of camshaft 700 in response to the rotation of locking knob 702 enables tee nut cam follower 704 to be raised by tee nut springs 712. This, in turn, causes tee nut 706 to be raised. Tee nut 706, in turn, grabs the flanges 801 of gun mount 100 and clamps flanges 801 against the bottom of carriage 412, thereby locking gun mount 100 against carriage 412. The rotation of camshaft 700 in response to moving locking knob 702 to a vertical position also allows secondary cam 714 (now driven down by secondary lock spring 802) and, thus, locking pilot pin 710 to lower down and engage gun mount 100, preventing gun mount 100 from being removed from carriage assembly 110.

To decouple gun mount and carriage assembly 110, locking knob 702 is moved from a vertical position to a horizontal position. Such movement causes locking pilot pin 710 to be raised, so that locking pilot pin 710 no longer engages gun mount 100. In addition, such movement also causes tee nut 706 to be lowered, thereby releasing the grip of tee nut 706 on gun mount 100. As a result of the foregoing, carriage assembly 110 can be slid away from gun mount 100.

FIGS. 7A, 7C, 8A, 8B and 8D illustrate a Y-axis offset feature. More specifically, gun mount 100 can be attached to carriage 412 via either of two tee slots 800 which are offset in the Y-axis. The two mounting positions defined by the Y-axis offset allow a biopsy needle to be positioned farther back from the chest wall of the patient. This advantageously accommodates a wider range of breast sizes, e.g., the offset position for larger breasts.

Figure 10A:
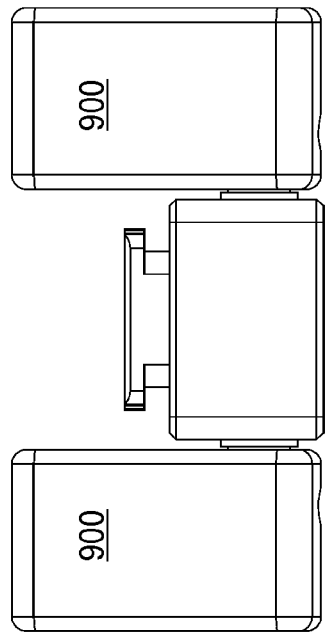
FIG. 10A is a top view of the X-axis stop of FIG. 9 shown in the unlocked position.
Figure 10B:
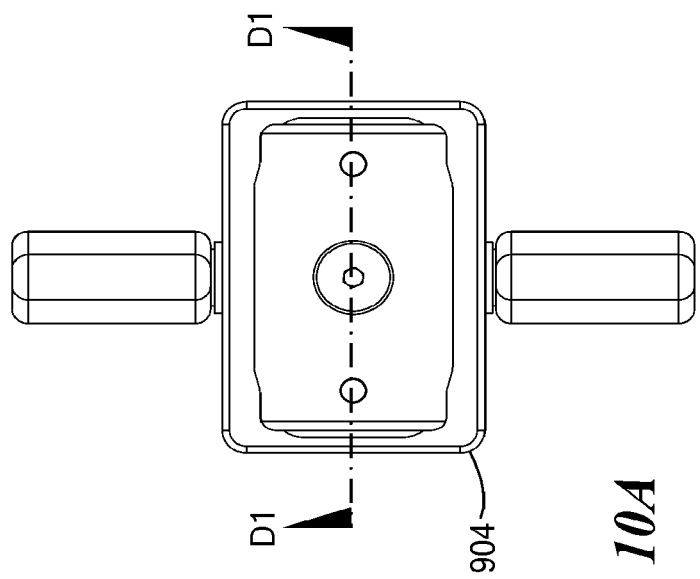
FIG. 10B is a cross-sectional view of the X-axis stop of FIG. 10A taken along section line D1-D1.
Figure 10C:
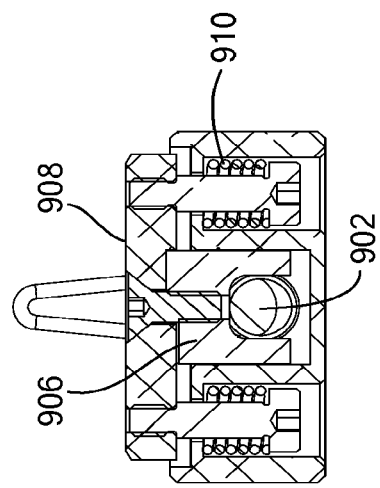
FIG. 10C is a side view of the X-axis stop of FIG. 9 in the unlocked position.
Figure 10D:
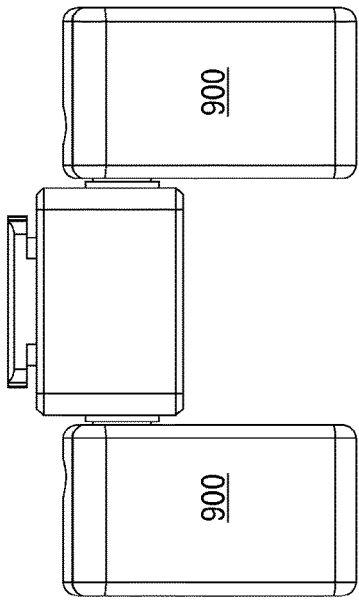
FIG. 10D is a top view of the X-axis stop of FIG. 9 in the locked position.
Figure 10F:
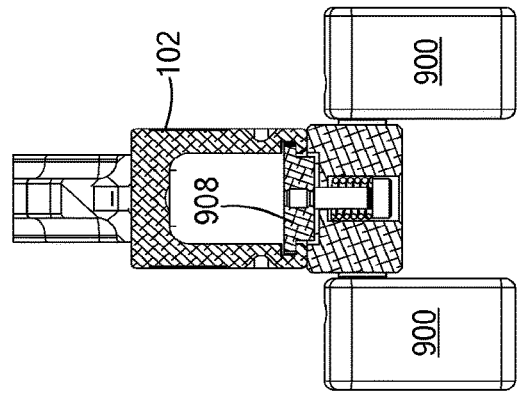
FIG. 10F is a side view of the X-axis stop of FIG. 9 in the locked position.
Figure 10E:
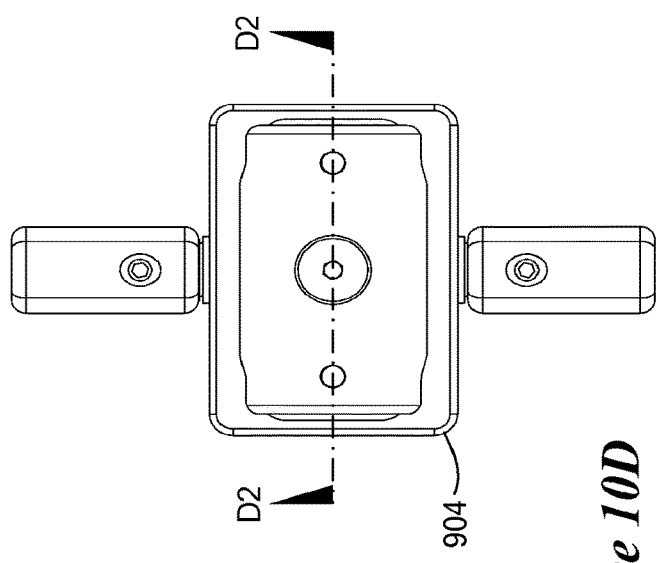
FIG. 10E is a cross-sectional view of the X-axis stop of FIG. 10D taken along section line D2-D2.
Figure 10G:
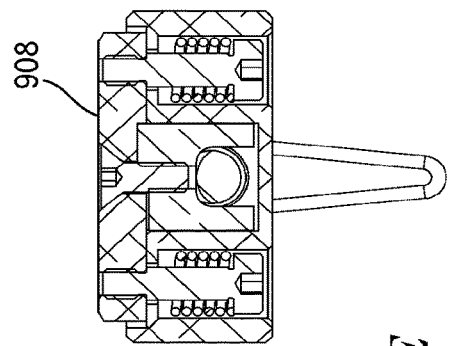
FIG. 10G is a section view showing the X-axis stop of FIG. 9 mounted on the lateral arm of FIG. 3.

Referring now to FIGS. 9, 10A, 10B, 10C, 10D, 10E and 10F, X-axis stop 152 is shown in greater detail. X-axis stop 152 may be removably mounted in bottom channel 401-2 of lateral arm 102 (see FIG. 10G) to provide a hard stop for delimiting x-axis movement of carriage assembly 110 relative to lateral arm 102. Corresponding locking knobs 900 are connected via a locking cam 902 which is disposed in an opening machined through the x-axis stop body 904. In the unlocked state specifically shown in FIGS. 10A, 10B and 10C, the locking knobs 900 are in the upper vertical position. In this position, the locking cam 902 exerts force against the locking cam follower 906, thereby lifting the tee nut 908 and compressing the locking springs 910. This is the highest operating position of the tee nut 908, which creates enough clearance between flanges of the tee nut and the X-axis stop body so that the assembly can be installed onto and move freely within a tee slot of the lateral arm 102. In the locked state specifically shown in FIGS. 10D, 10E and 10F, the locking knobs 900 are in the lower vertical position (rotated 180 degrees relative to the unlocked position). In this position, the locking cam 902 is no longer applying force against the locking cam follower 906 so the locking springs 910 are free to retract the tee nut 908 toward the X-axis stop body 904, thereby clamping against lateral arm 102. Note that the likelihood of premature wear due to excess clamping force is mitigated by use of the locking springs rather than direct pressure from the knobs.

Figure 11:
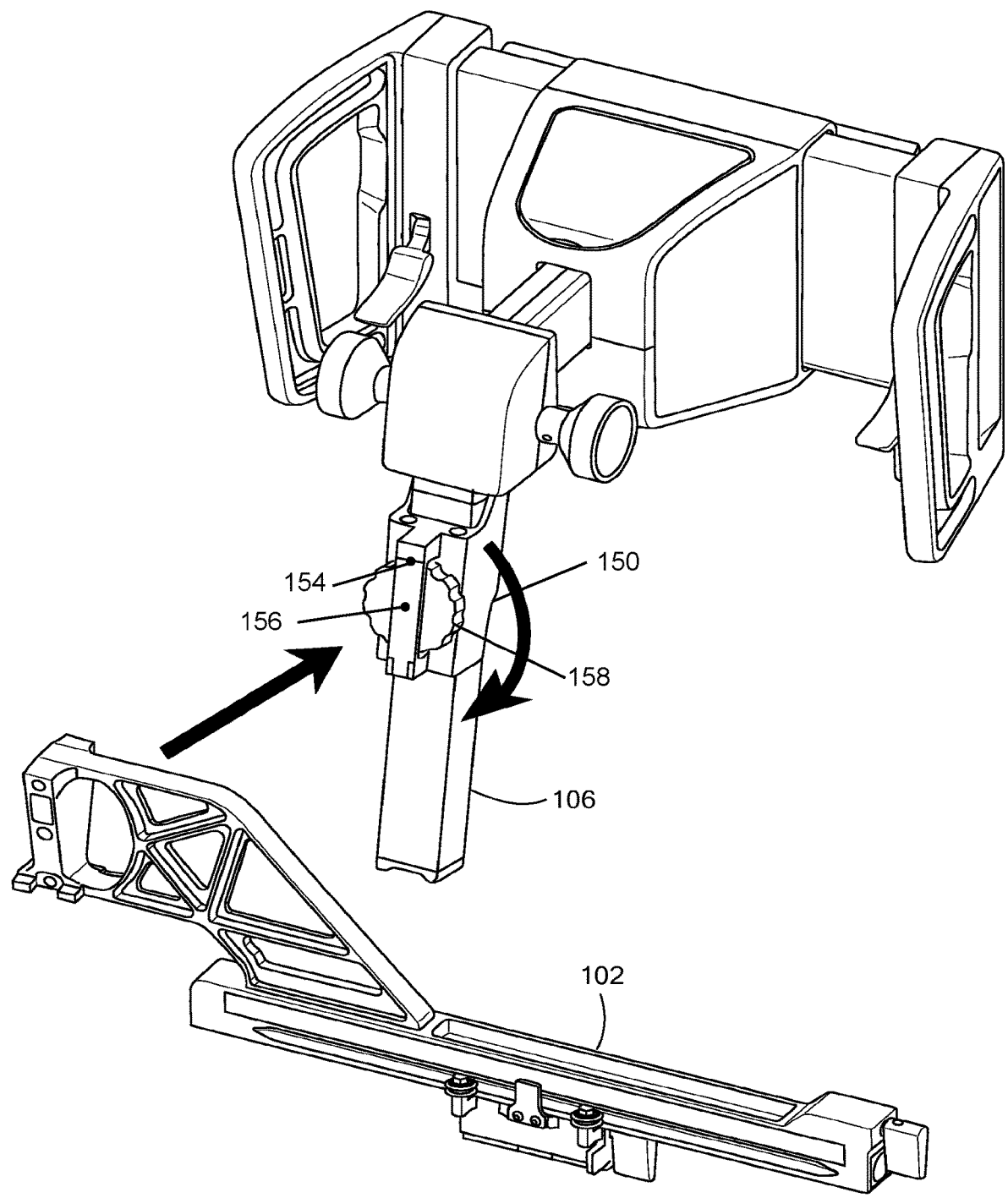
FIGS. 11 through 18 illustrate various configurations of the lateral arm needle guide and assembly steps of various components.
Figure 12:
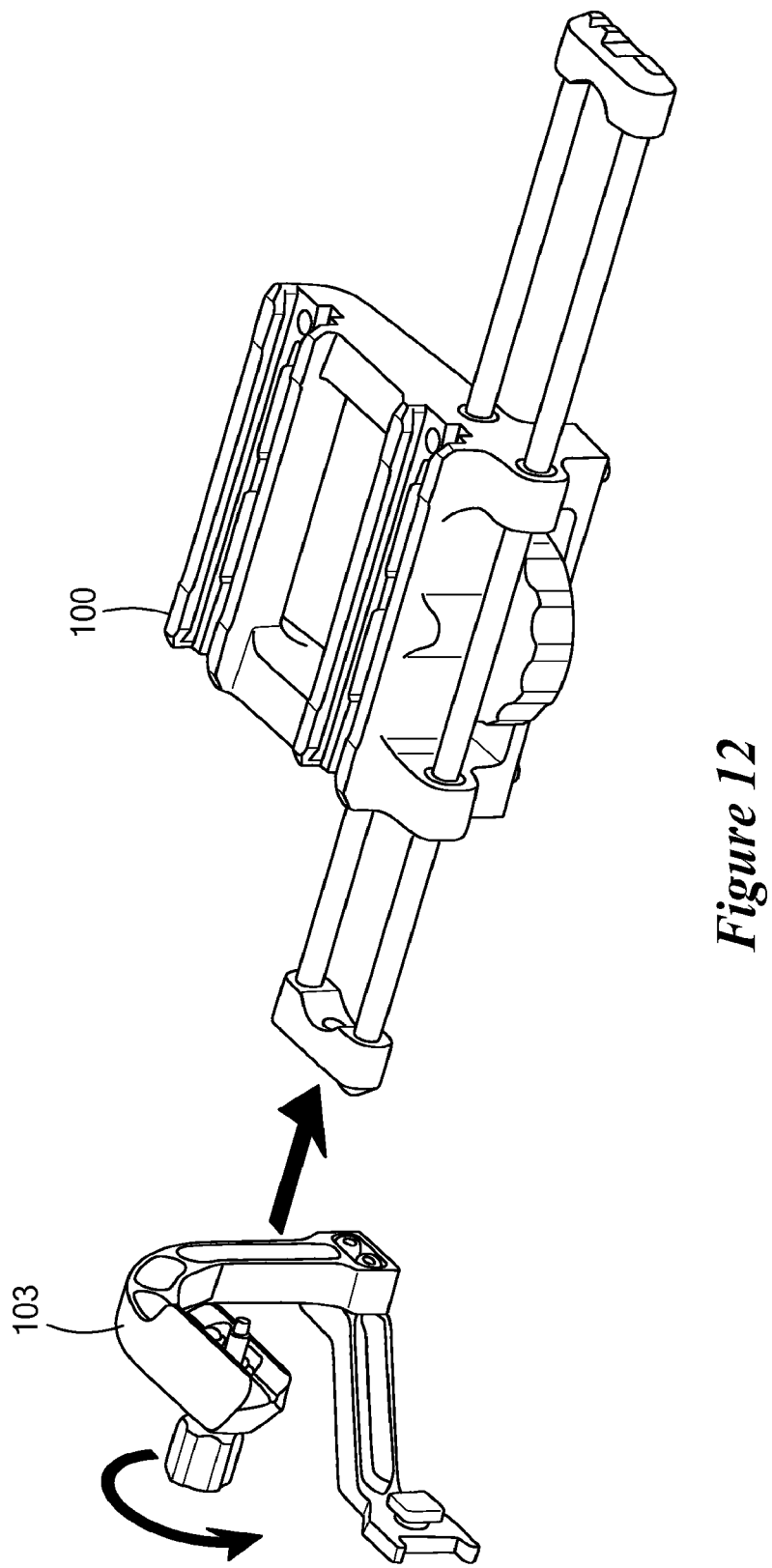
Figure 13:
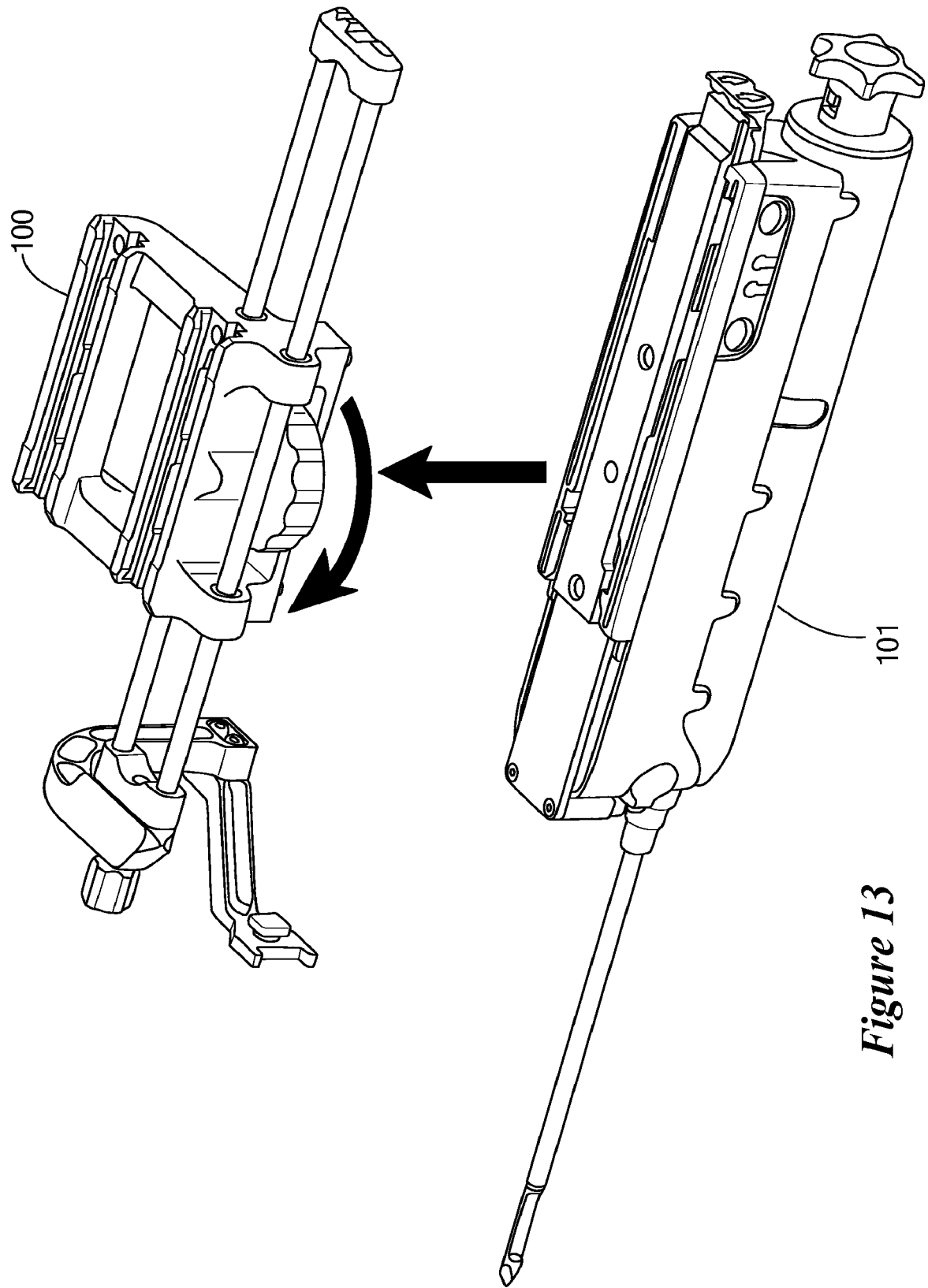
Figure 14:
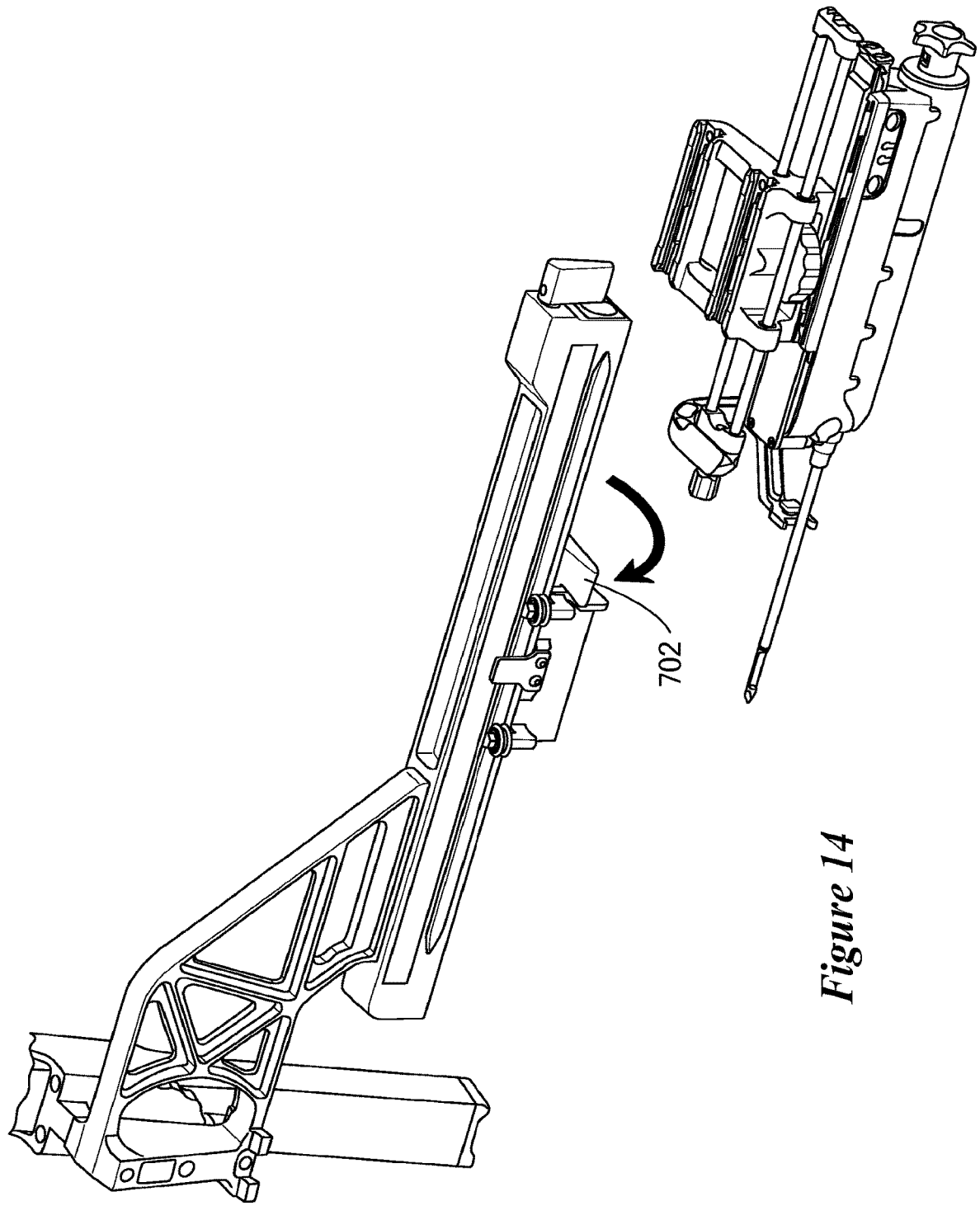
Figure 15:
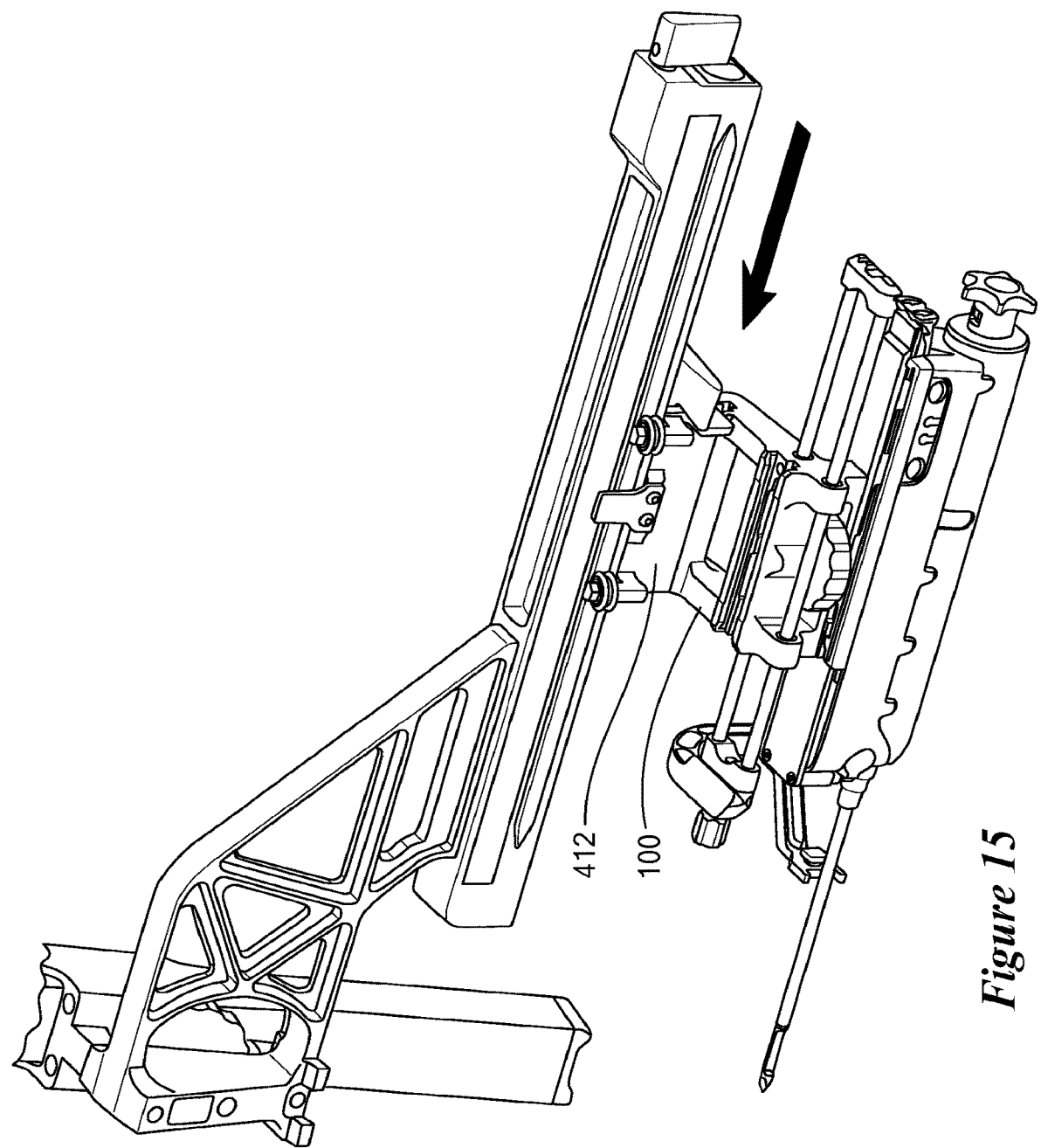
Figure 16:
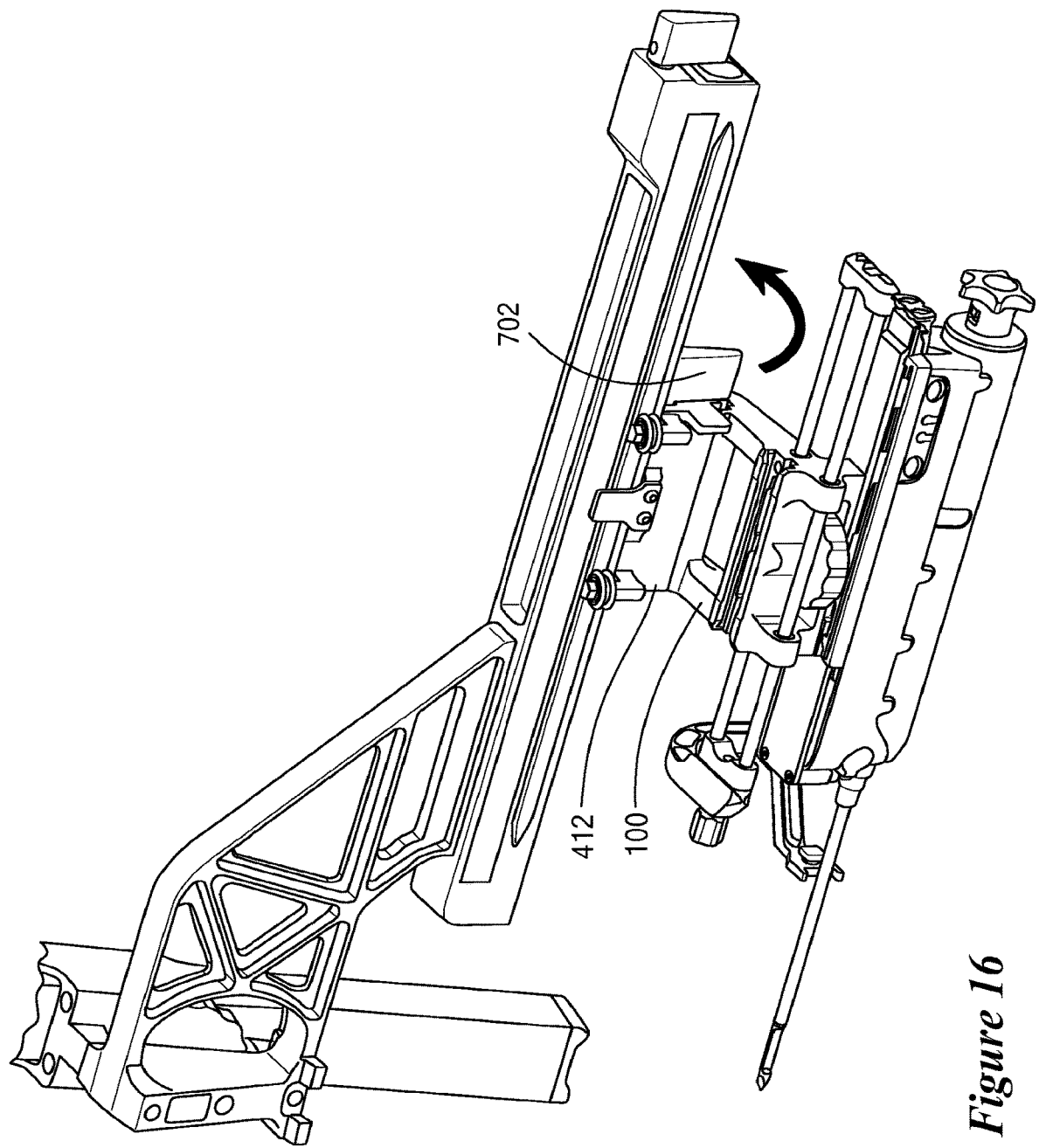
Figure 17:
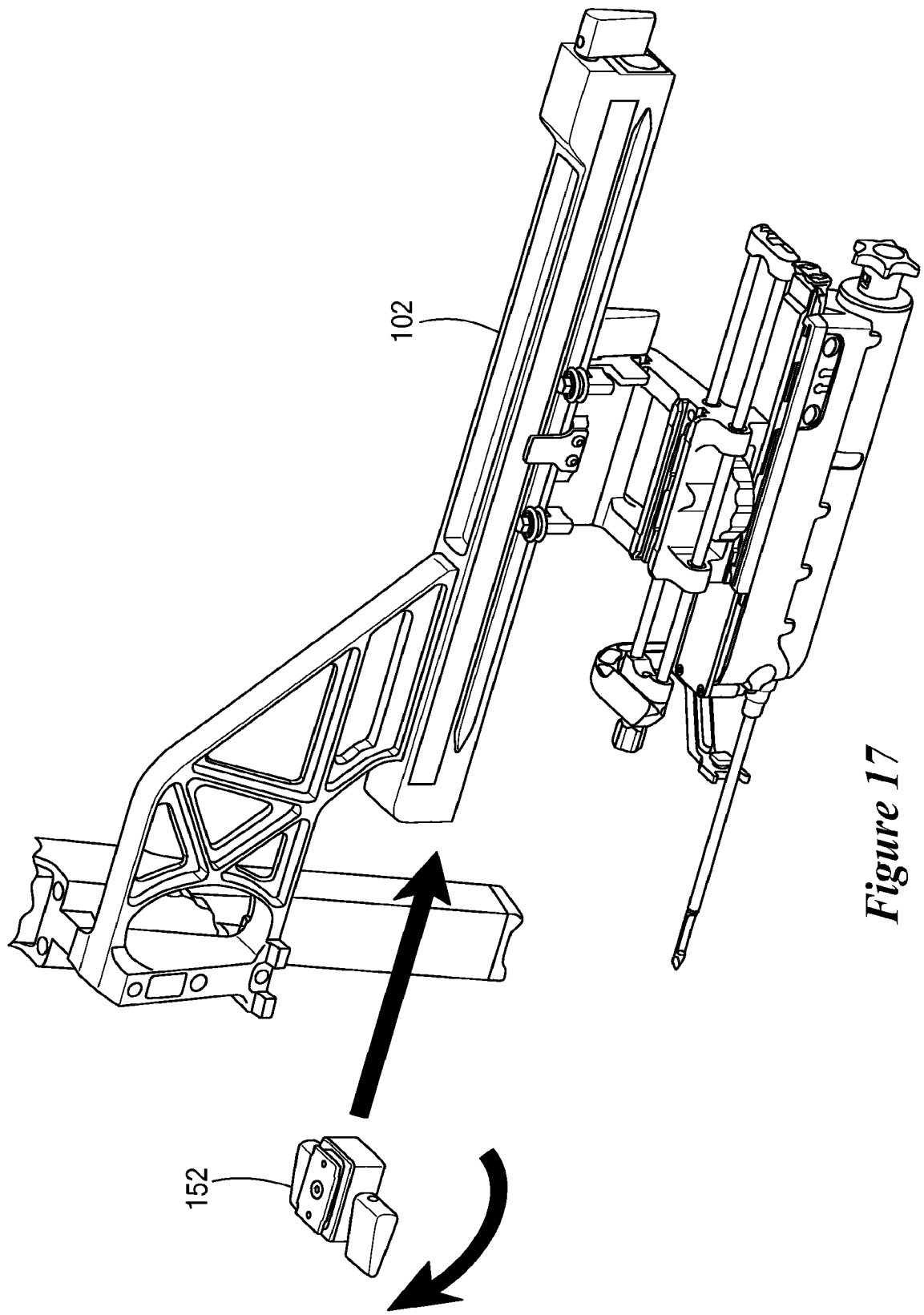
Figure 18:
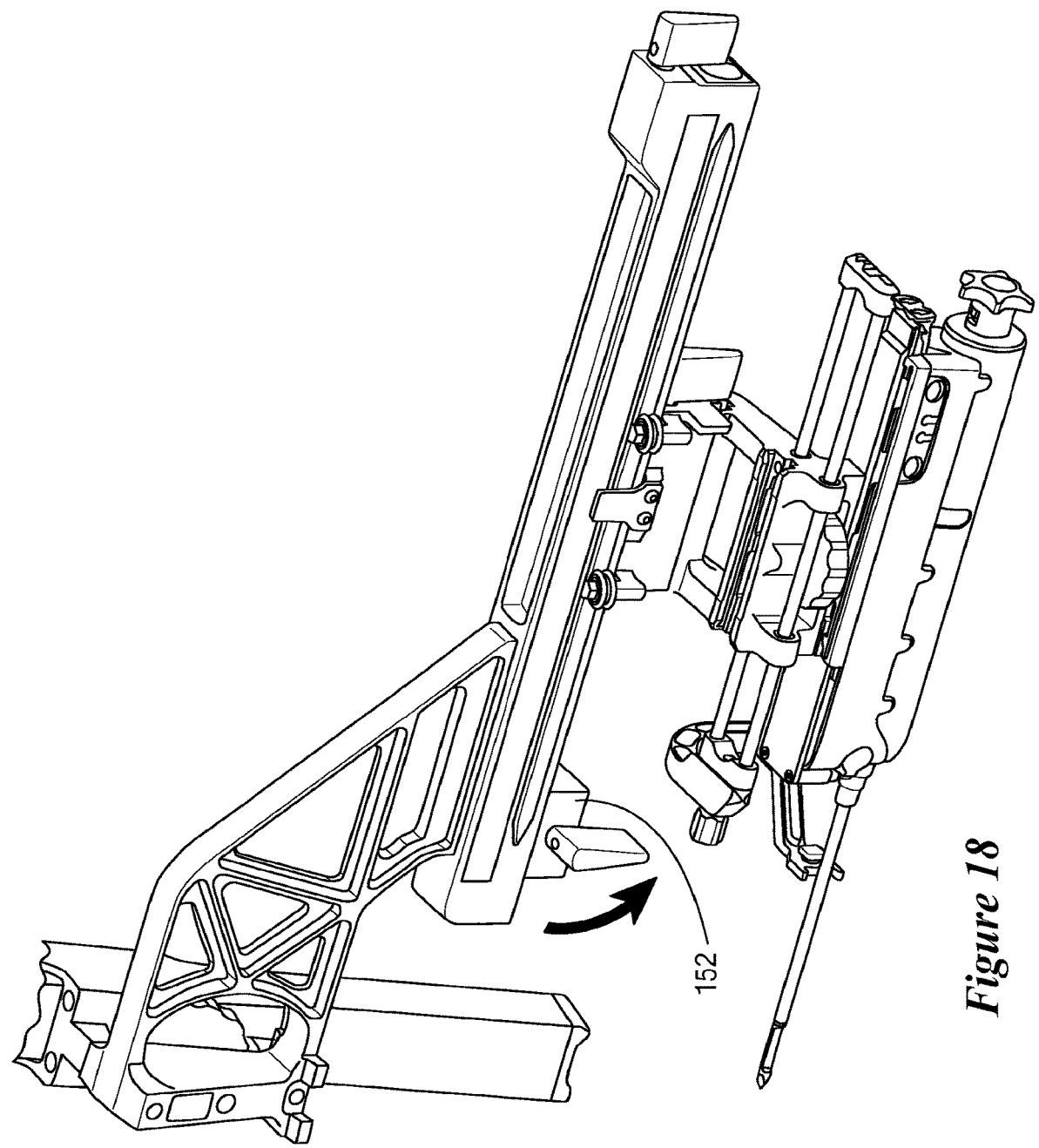

FIGS. 11 through 18 illustrate various configurations of the lateral arm needle guide and assembly steps of various components. FIG. 11 shows lateral arm 102 being secured to post member 106. The clamp member 150 includes guide posts 154 and a threaded fastening member 156 actuated by a knob 158 for positioning and securing the clamp member relative to the lateral arm 102. The lateral arm includes corresponding smooth and threaded sockets for receiving the guide posts and threaded fastening member. FIG. 12 shows needle guide 103 being attached to gun mount 100. FIG. 13 shows biopsy needle gun 101 being attached to gun mount 100. FIG. 14 shows gun mount locking knob 702 being positioned in the disengaged state. FIG. 15 shows gun mount 100 being slid into a mounted position with respect to carriage 412. FIG. 16 shows gun mount locking knob 702 being positioned in the engaged state, thereby securing gun mount 100 to carriage 412. FIG. 17 shows X-axis stop 152 being positioned in the disengaged state and mounted onto lateral arm 102. FIG. 18 shows X-axis stop 152 being positioned in the engaged state, thereby securing it in position relative to the lateral arm 102.

While the invention has been described through the above examples and features, it will be understood by those of ordinary skill in the art that a wide variety of modifications, combinations and variations of the examples and features may be made without departing from the inventive concepts herein disclosed. Moreover, the invention should not be viewed as being limited to any specific purposes described herein, but rather should be viewed as being applicable to accomplish a wide variety of purposes beyond those described herein.

The invention claimed is:

1. A biopsy guidance module for attachment to a breast imaging system comprising a breast support platform, the biopsy guidance module comprising:
    a module body for securement to the breast imaging system;
    a post member extending from the module body at an angle;
    a clamp member disposed directly around and slidably positionable along the length of the post member, wherein the clamp member is configured to secure directly to the post at a plurality of different positions along the length of the post member, and wherein the clamp member has a front face configured to face away from the breast imaging system, the front face supporting an attachment mechanism for coupling one or more components to the clamp member, the attachment mechanism includes a knob having a threaded fastening member projecting outward from the front face and at least one guide post;
    a gun mount movably secured relative to the post member; and
    a biopsy gun secured to the gun mount.

2. The biopsy guidance module of claim 1, further comprising a rail and a carriage disposed between the clamp member and the gun mount, wherein the carriage comprises a plurality of rollers for positionably engaging the gun mount along a length of the rail.

3. The biopsy guidance module of claim 2, wherein the rail is disposed at an angle to the post member and a needle of the biopsy gun is disposed parallel to the rail.

4. The biopsy guidance module of claim 1, wherein a needle of the biopsy gun is disposed substantially parallel to a front surface of the breast support platform when movably secured to the post member.

5. The biopsy guidance module of claim 4, wherein the needle of the biopsy gun is disposed parallel to a top surface of the breast support platform when movably secured to the post member.

6. The biopsy guidance module of claim 1, further comprising a computer that determines at least one characteristic of the biopsy gun based on an operator input.

7. The biopsy guidance module of claim 1, wherein the biopsy guidance module is positionable relative to the breast support platform.

8. The biopsy guidance module of claim 7, wherein the biopsy guidance module is positionable vertically relative to the breast support platform.

\* \* \* \* \*